(12) United States Patent
Yamashita

(10) Patent No.: US 12,303,367 B2
(45) Date of Patent: May 20, 2025

(54) ATTACHABLE-TYPE DISPOSABLE WEARING ARTICLE

(71) Applicant: DAIO PAPER CORPORATION, Ehime (JP)

(72) Inventor: Yuichi Yamashita, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 464 days.

(21) Appl. No.: 17/911,748

(22) PCT Filed: Mar. 9, 2021

(86) PCT No.: PCT/JP2021/009195
§ 371 (c)(1),
(2) Date: Sep. 15, 2022

(87) PCT Pub. No.: WO2021/192999
PCT Pub. Date: Sep. 30, 2021

(65) Prior Publication Data
US 2023/0120091 A1  Apr. 20, 2023

(30) Foreign Application Priority Data

Mar. 25, 2020 (JP) .................................. 2020-054784

(51) Int. Cl.
*A61F 13/15* (2006.01)
*A61F 13/494* (2006.01)

(52) U.S. Cl.
CPC .. *A61F 13/49466* (2013.01); *A61F 13/49473* (2013.01); *A61F 2013/4948* (2013.01)

(58) Field of Classification Search
CPC .......... A61F 13/49466; A61F 13/49473; A61F 13/49406; A61F 13/494; A61F 13/49413; A61F 2013/4948

(Continued)

(56) References Cited

U.S. PATENT DOCUMENTS

| | | | | |
|---|---|---|---|---|
| 7,300,427 B2 * | 11/2007 | Sugito | ................... | A61F 13/565 604/385.27 |
| 2016/0270983 A1 * | 9/2016 | Roe | .................. | A61F 13/49007 |
| 2017/0000658 A1 * | 1/2017 | Chatterjee | ......... | A61F 13/49011 |

FOREIGN PATENT DOCUMENTS

| | | |
|---|---|---|
| JP | 2001-061888 | 3/2001 |
| JP | 2005-161006 | 6/2005 |

(Continued)

OTHER PUBLICATIONS

International Search Report for PCT/JP2021/009195, dated May 25, 2021.

*Primary Examiner* — Jacqueline F Stephens
(74) *Attorney, Agent, or Firm* — Andrus Intellectual Property Law, LLP

(57) ABSTRACT

An attachable-type disposable wearing article including waist elastic members fixed to an end flap, standup gather parts located on opposed widthwise sides, a linear first bending part extending in the width direction from a front edge of one of the back laid-down portions to a front edge of the other, and a linear second bending part extending in the width direction and spaced forwardly apart from the first bending part, a first area adjacent backward to the first bending part and a second area between the first and second bending parts, the waist stretchable region is provided at least between the opposed right and left back laid-down portions, and the first bending part has lower rigidity compared to the first area and the second area.

14 Claims, 26 Drawing Sheets

(58) Field of Classification Search
USPC ............ 604/385.28, 385.24, 385.27, 385.29, 604/385.3
See application file for complete search history.

(56) References Cited

FOREIGN PATENT DOCUMENTS

| | | |
|---|---|---|
| JP | 2016-010442 | 1/2016 |
| JP | 2017-64169 | 4/2017 |
| JP | 2019-71956 | 5/2019 |
| WO | 2015/198928 | 12/2015 |

\* cited by examiner

[FIG.1]
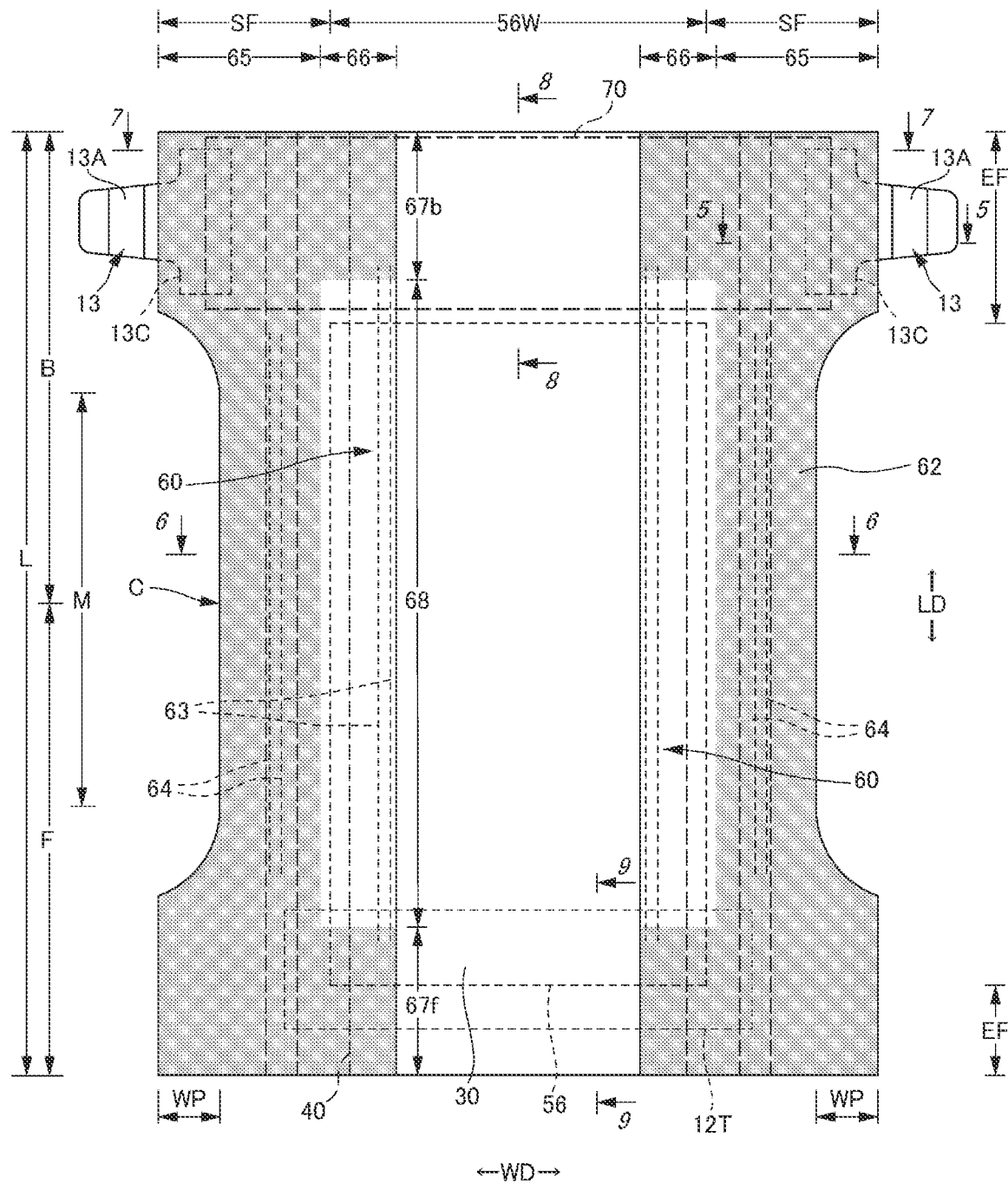

[FIG.2]
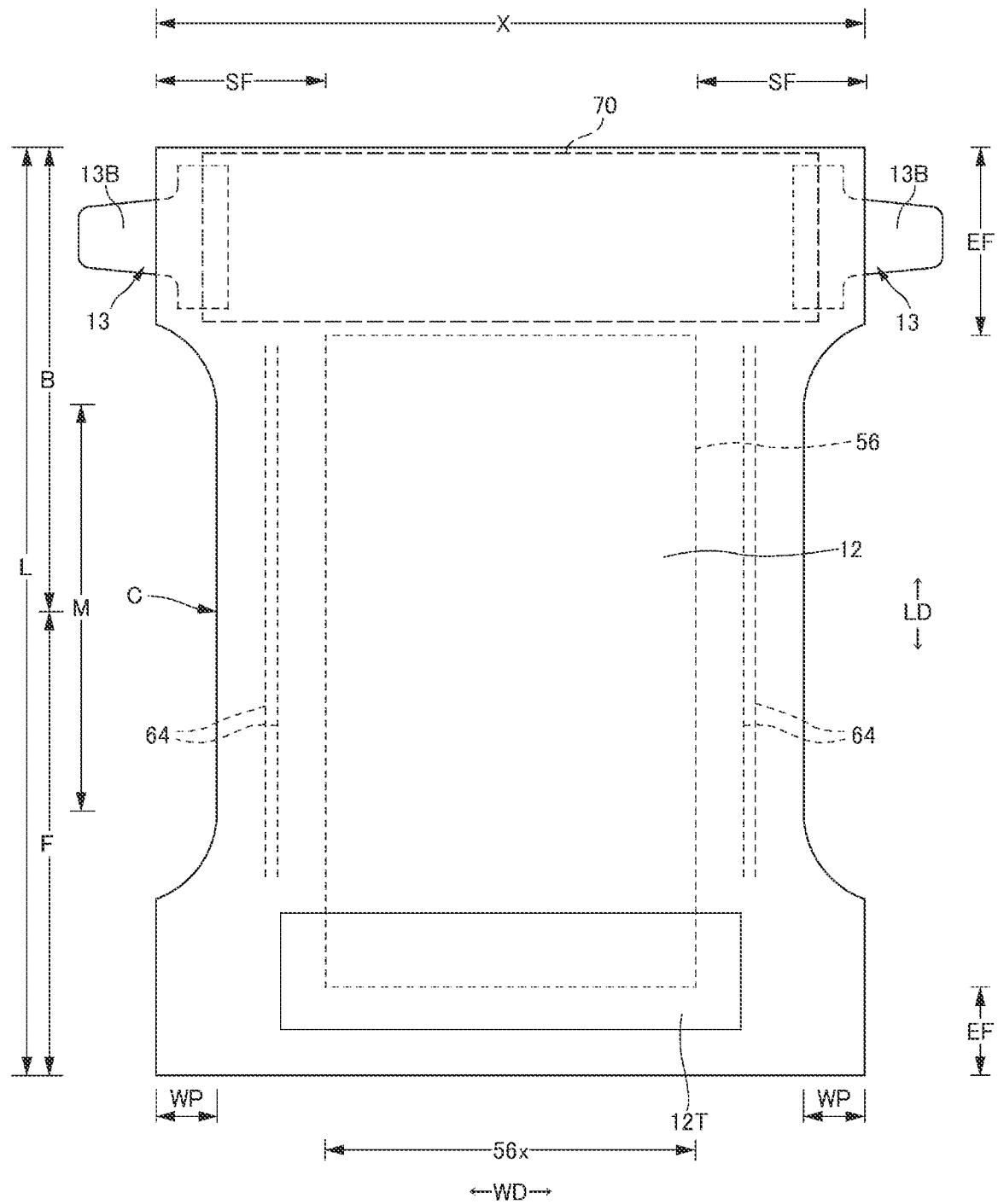

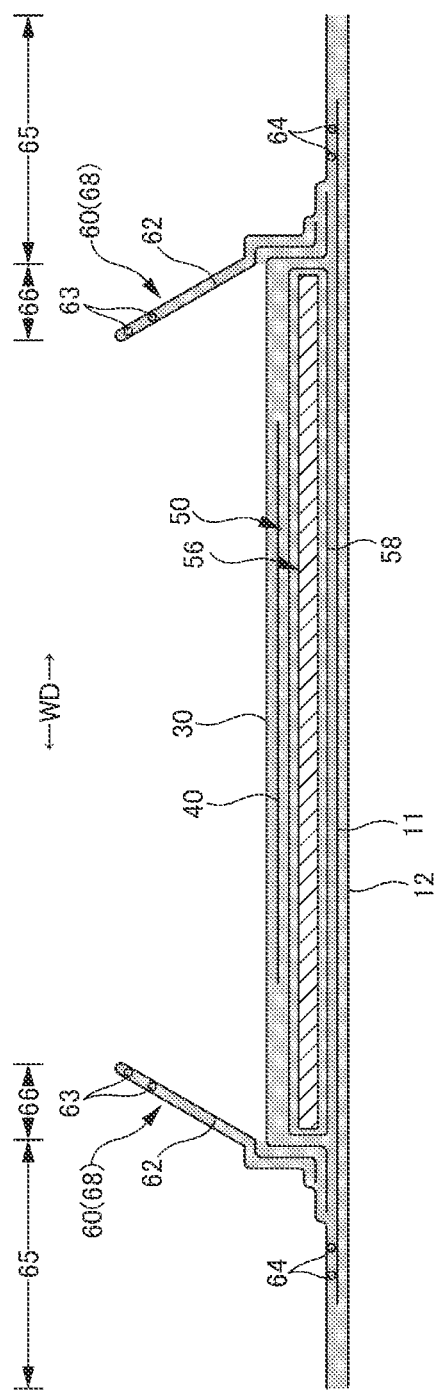

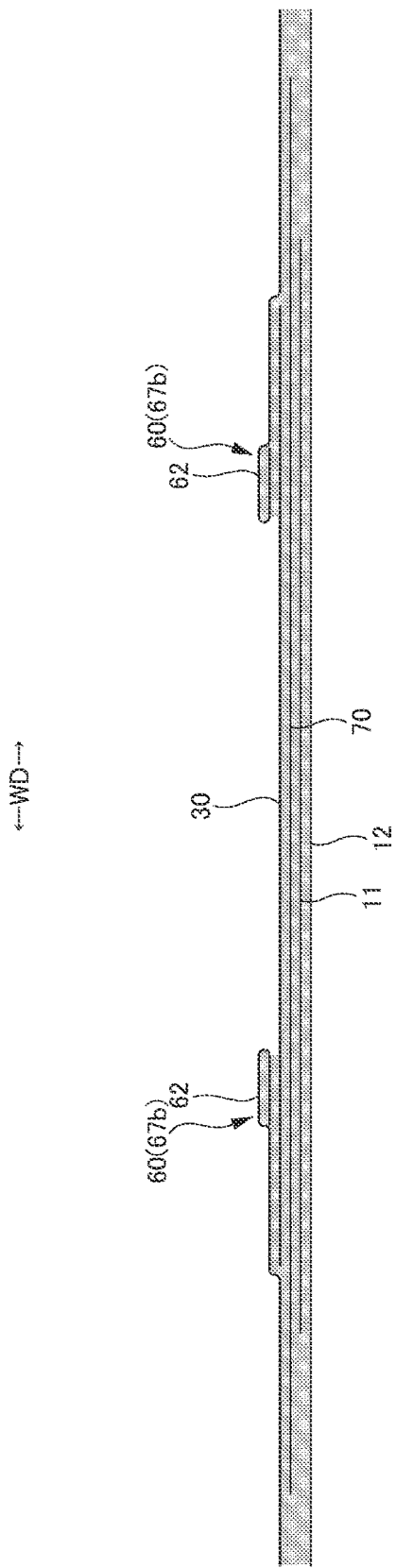
[FIG.4]

[FIG.5]
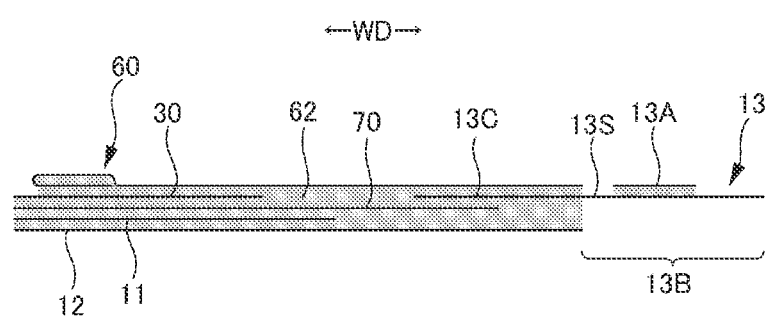

[FIG.6]
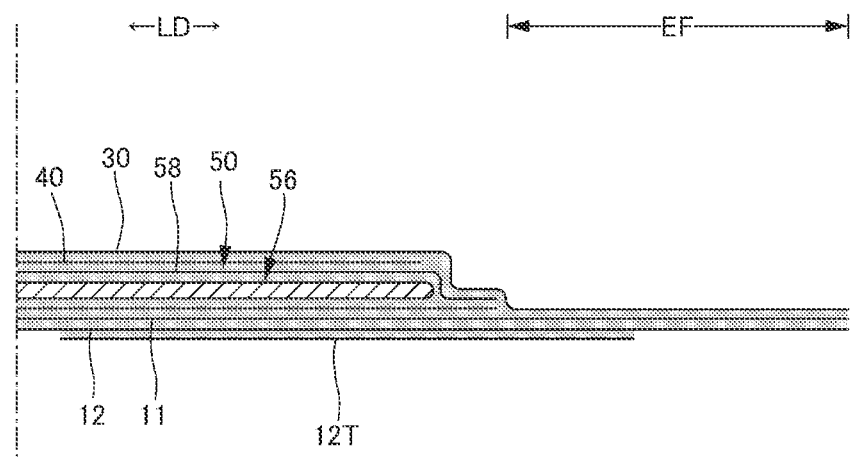

[FIG.7]
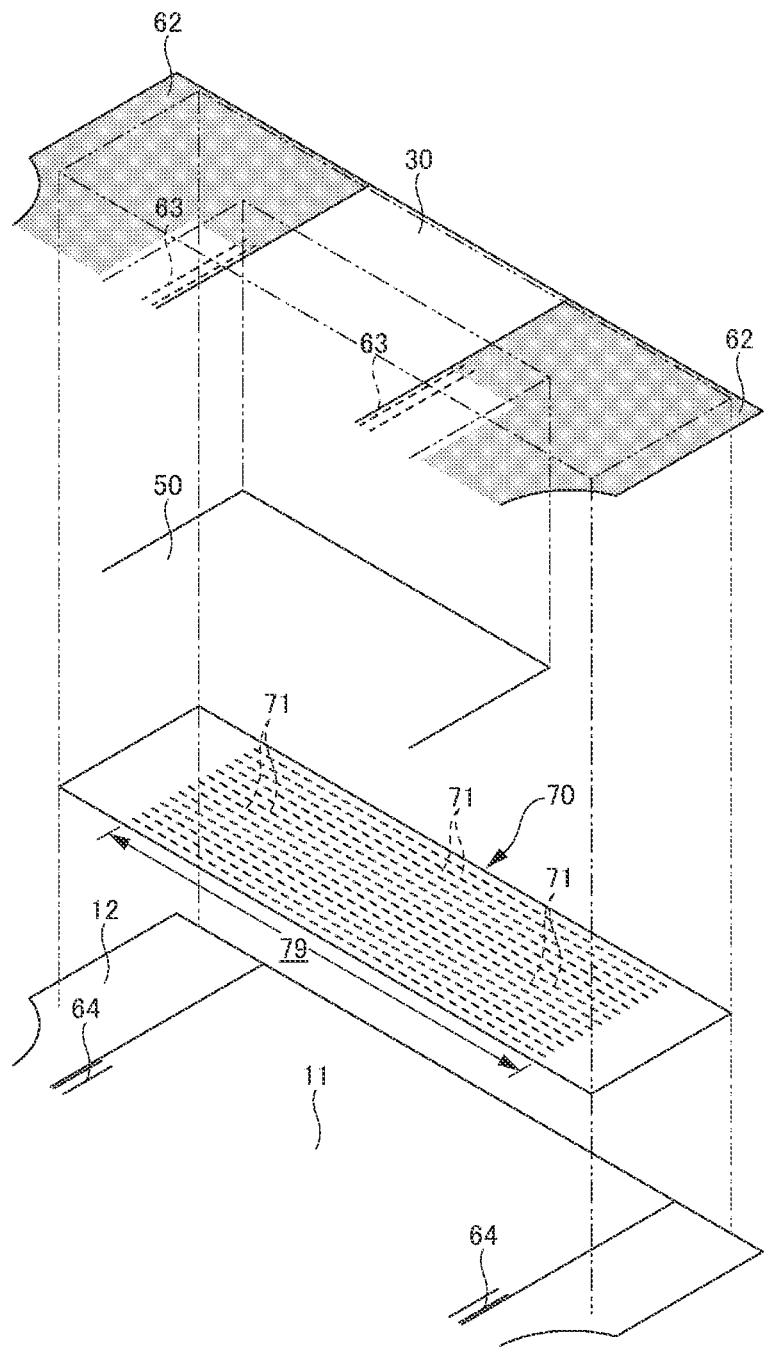

[FIG.8]
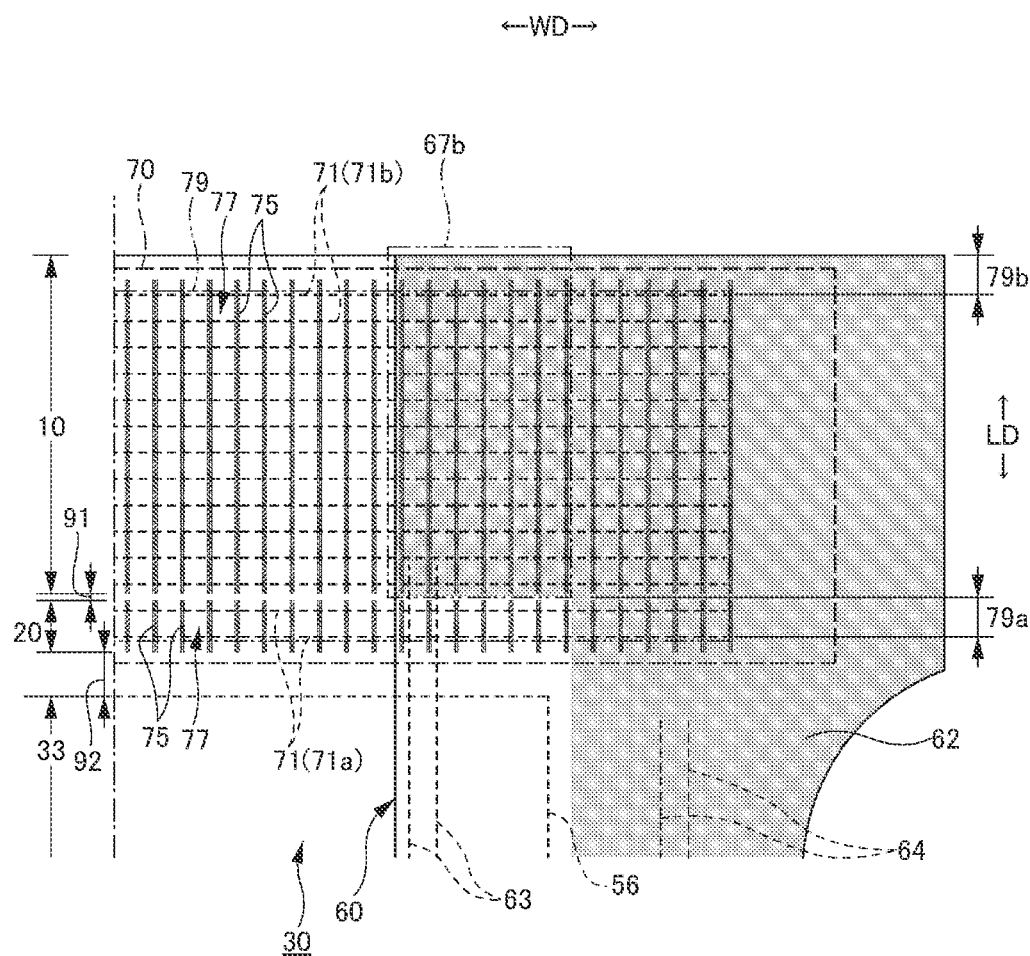

[FIG.9]
(a)
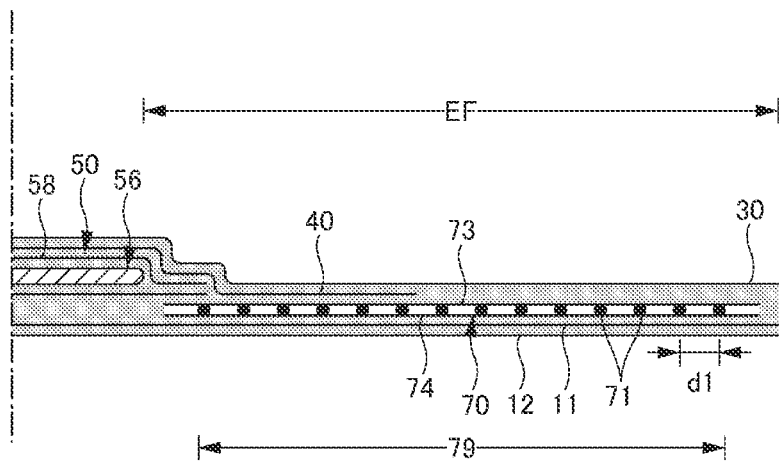
(b)
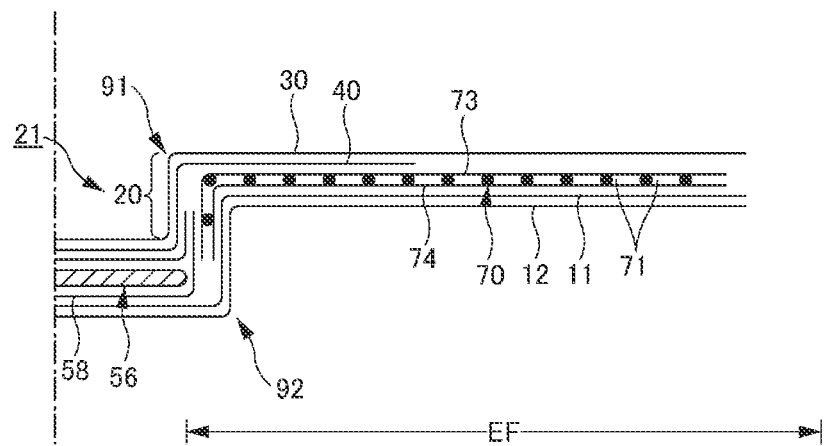

[FIG.10]
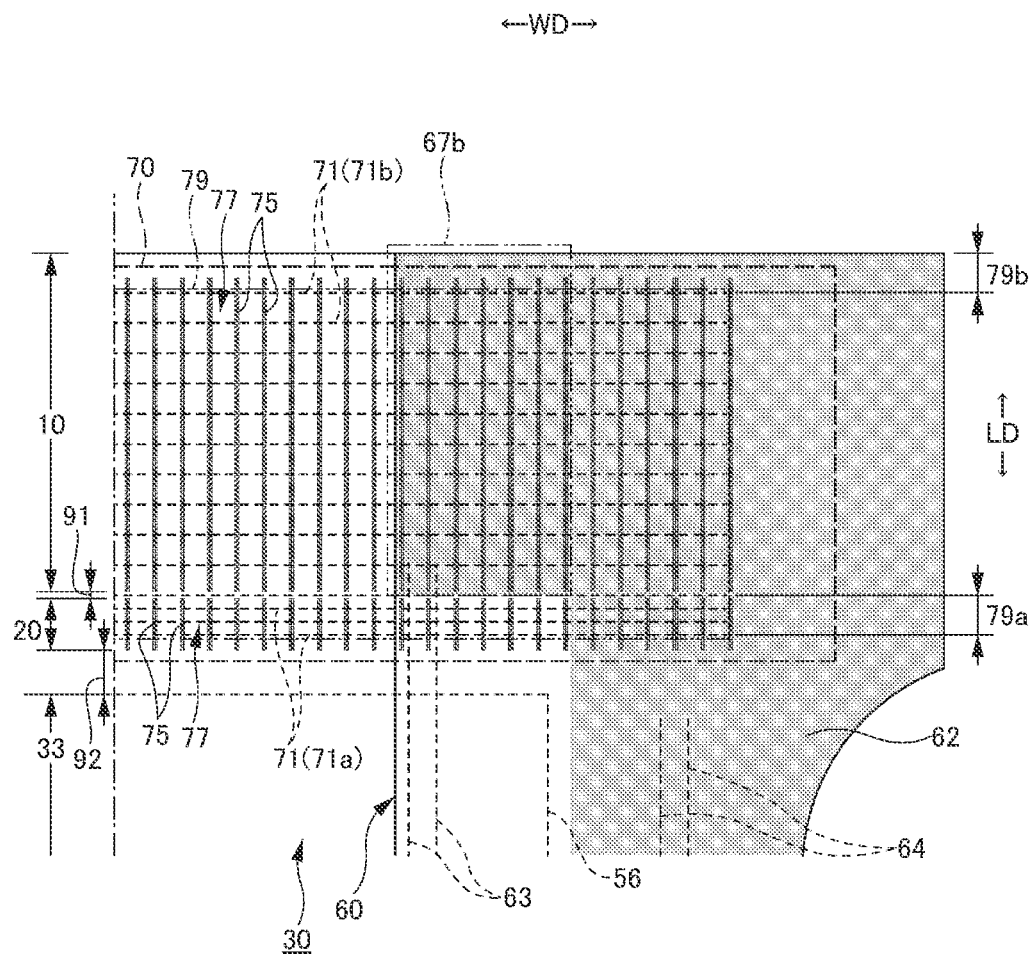

[FIG.11]
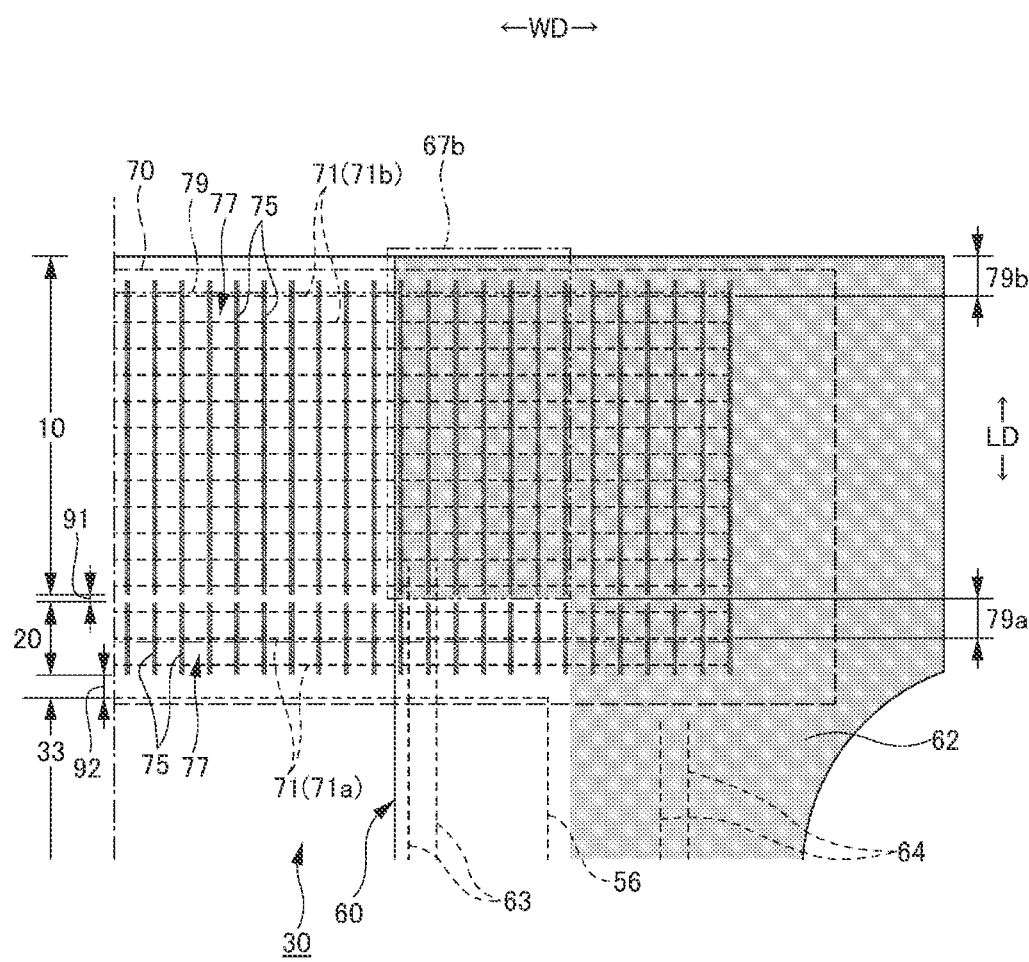

[FIG.12]
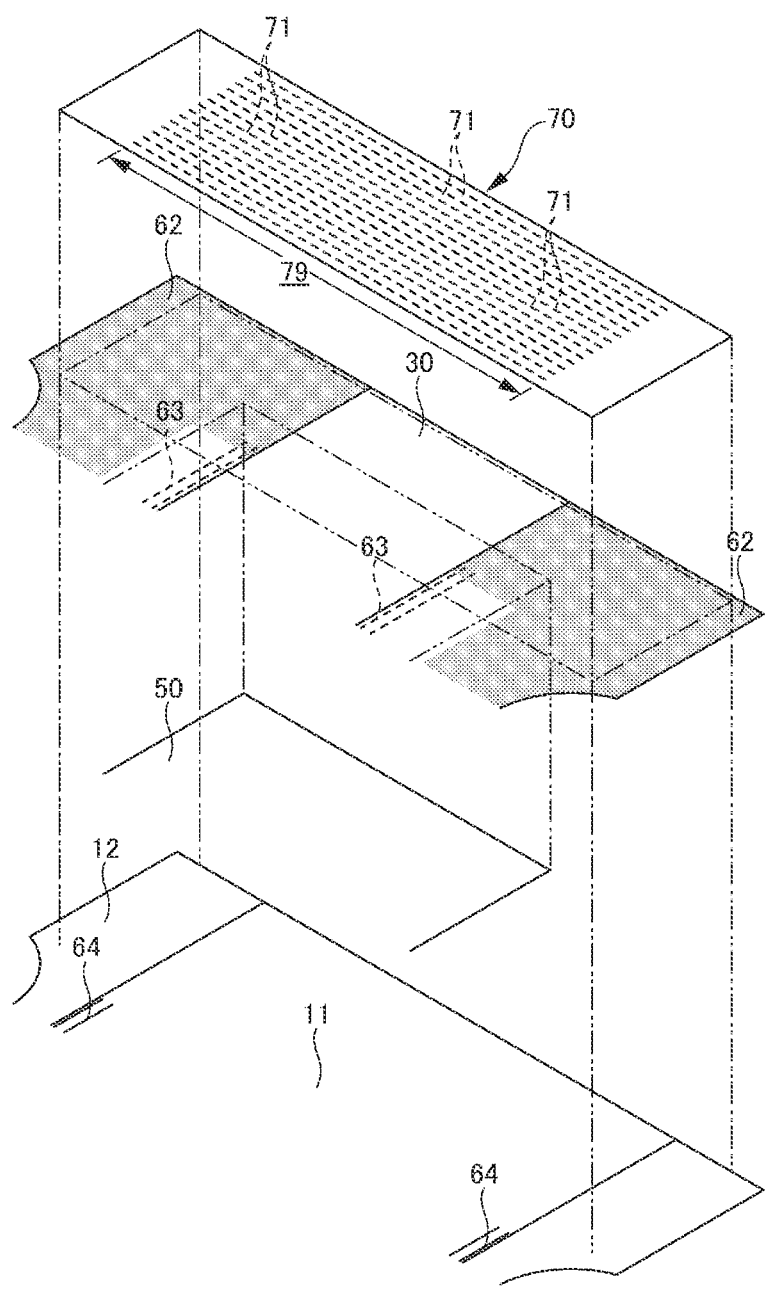

[FIG.13]
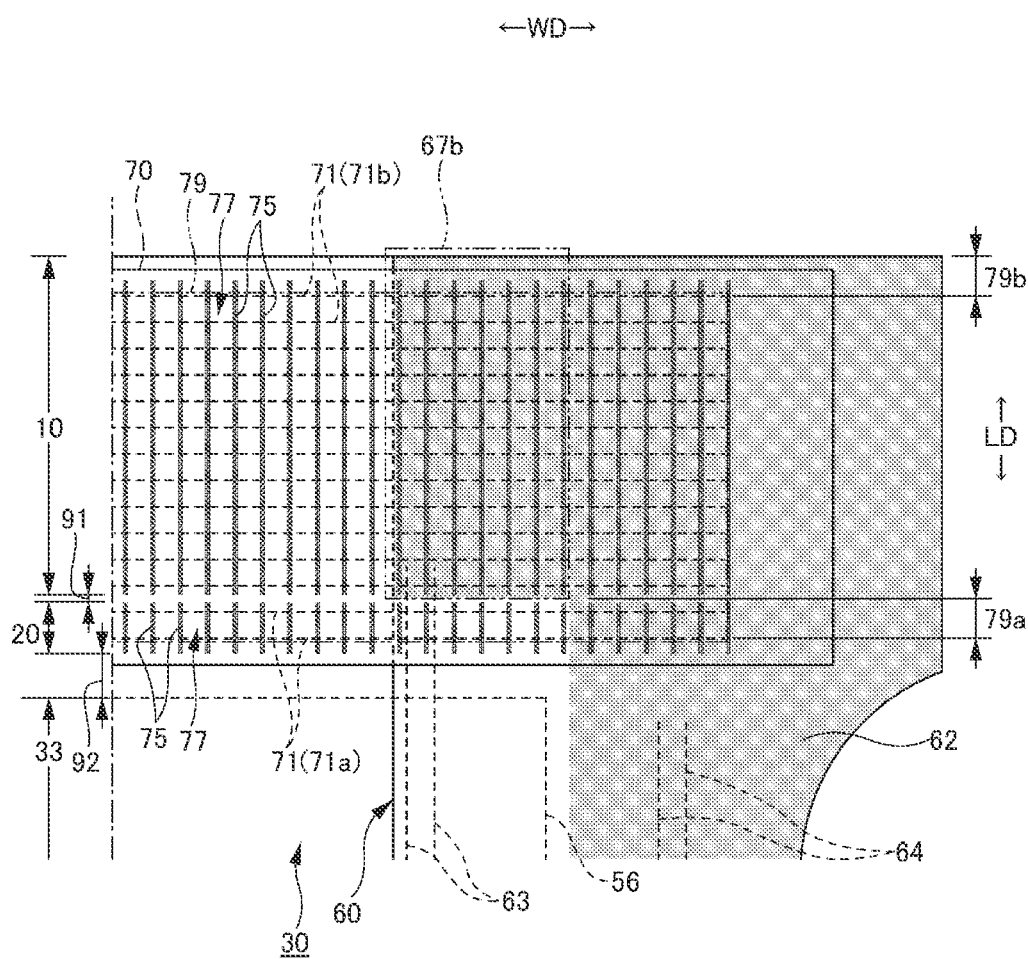

[FIG.14]
(a)
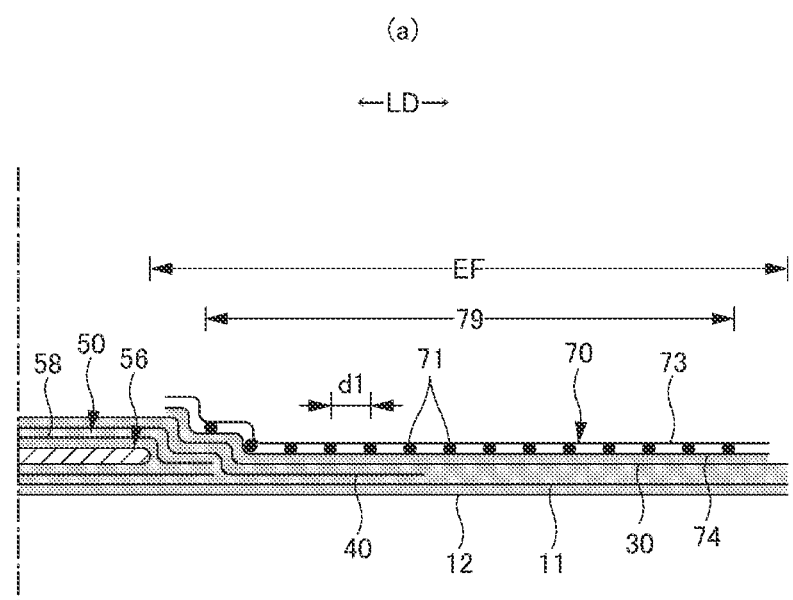
(b)
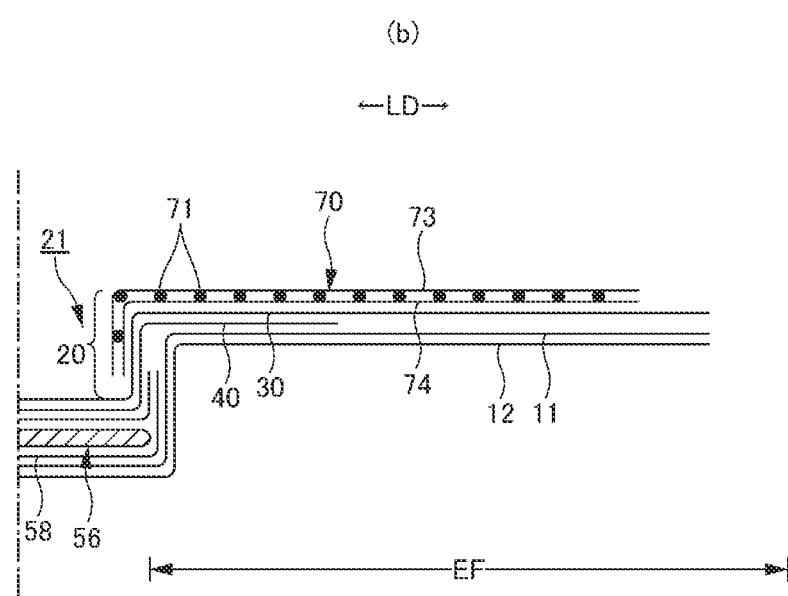

[FIG.15]
(a)
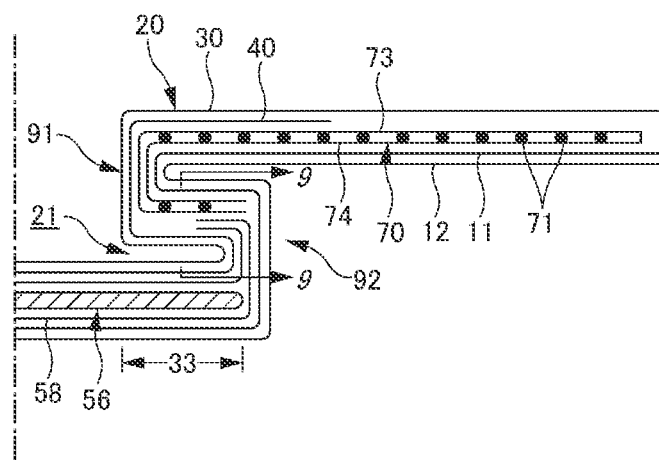
(b)
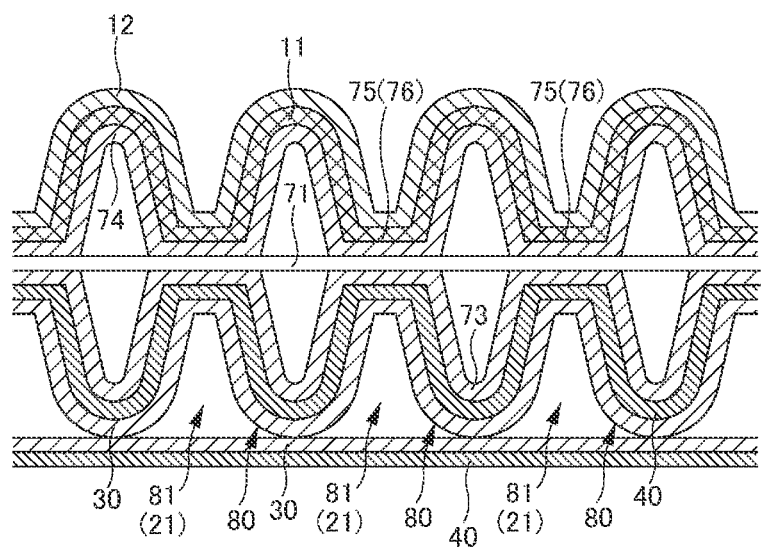

[FIG.16]
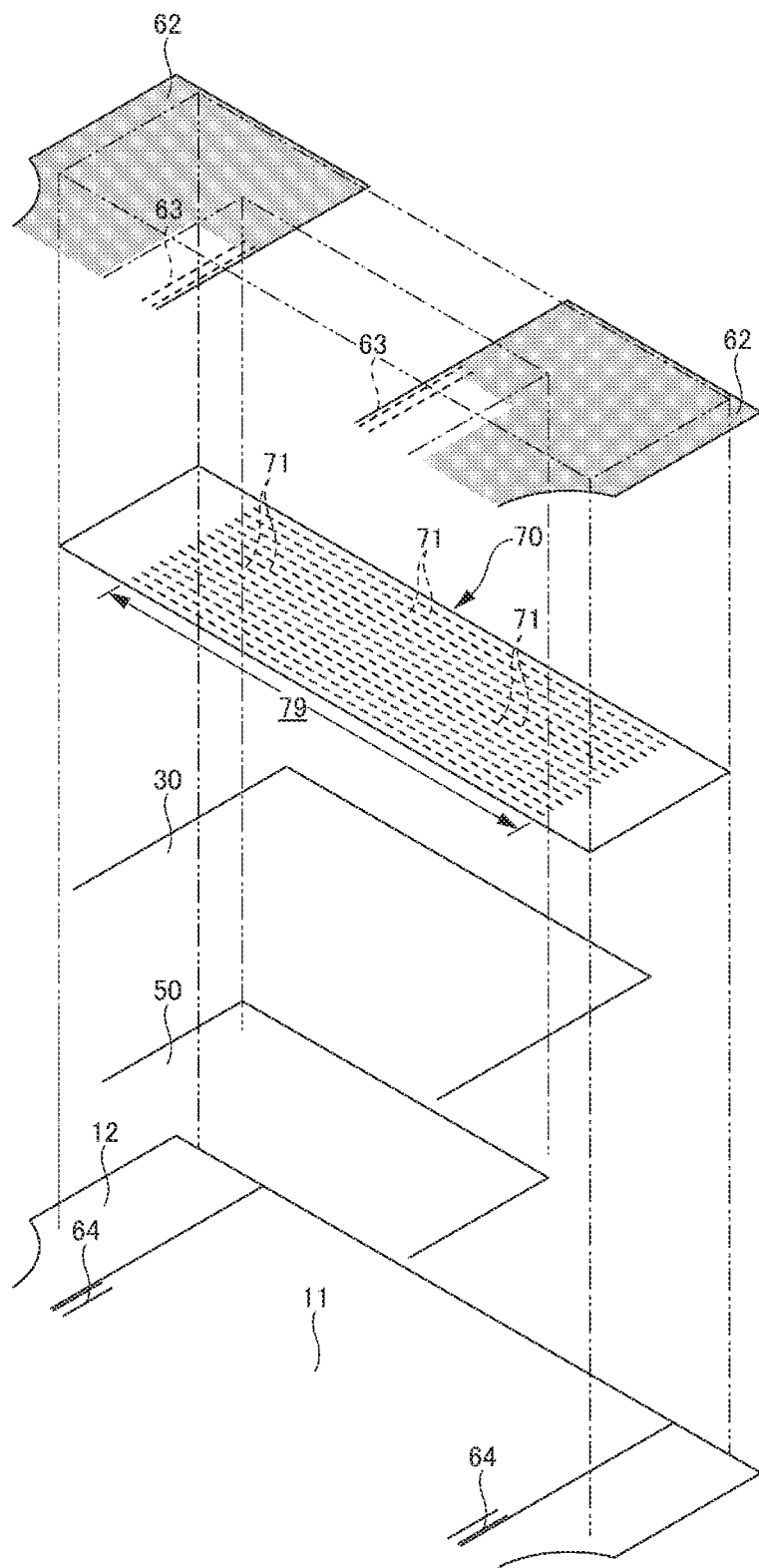

[FIG.17]
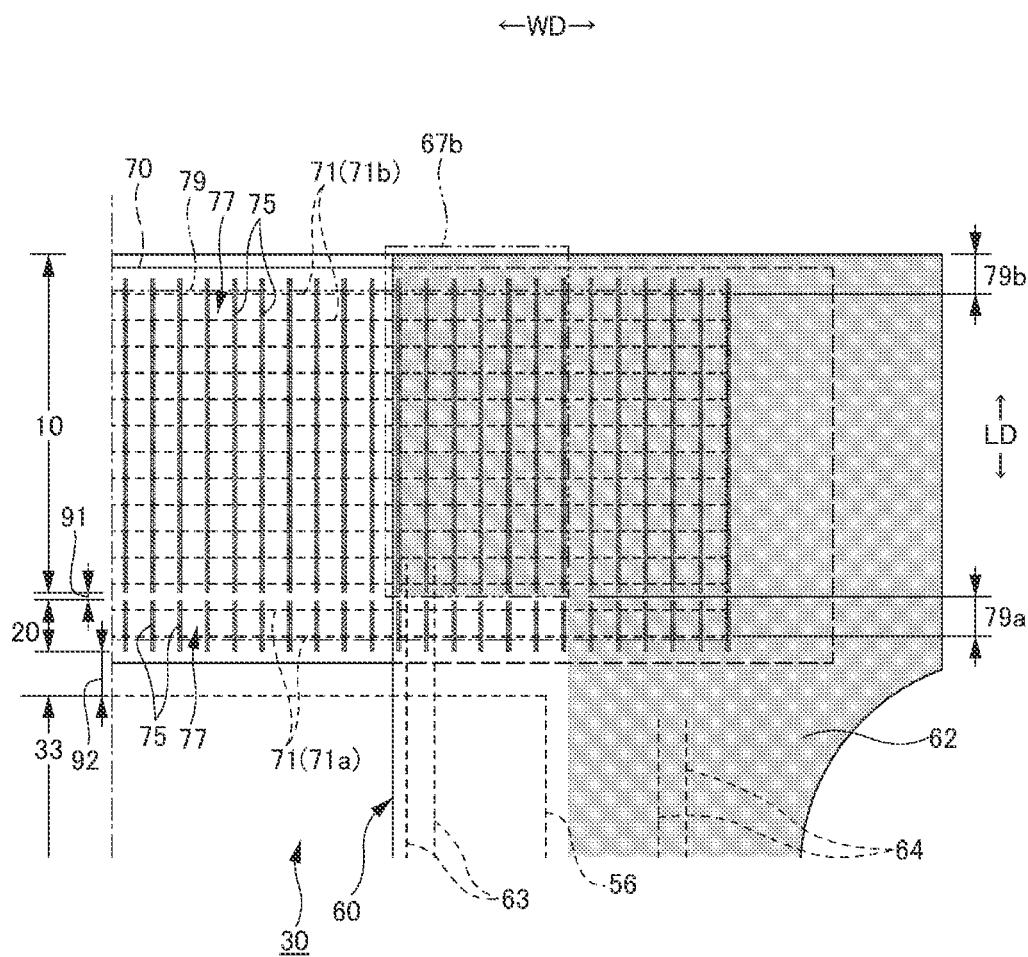

[FIG.18]
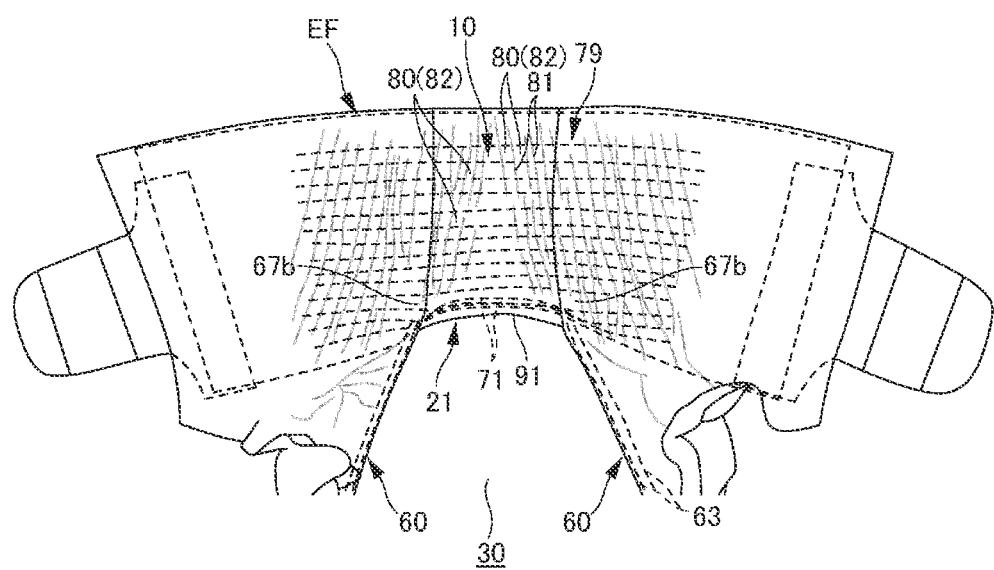

[FIG.19]
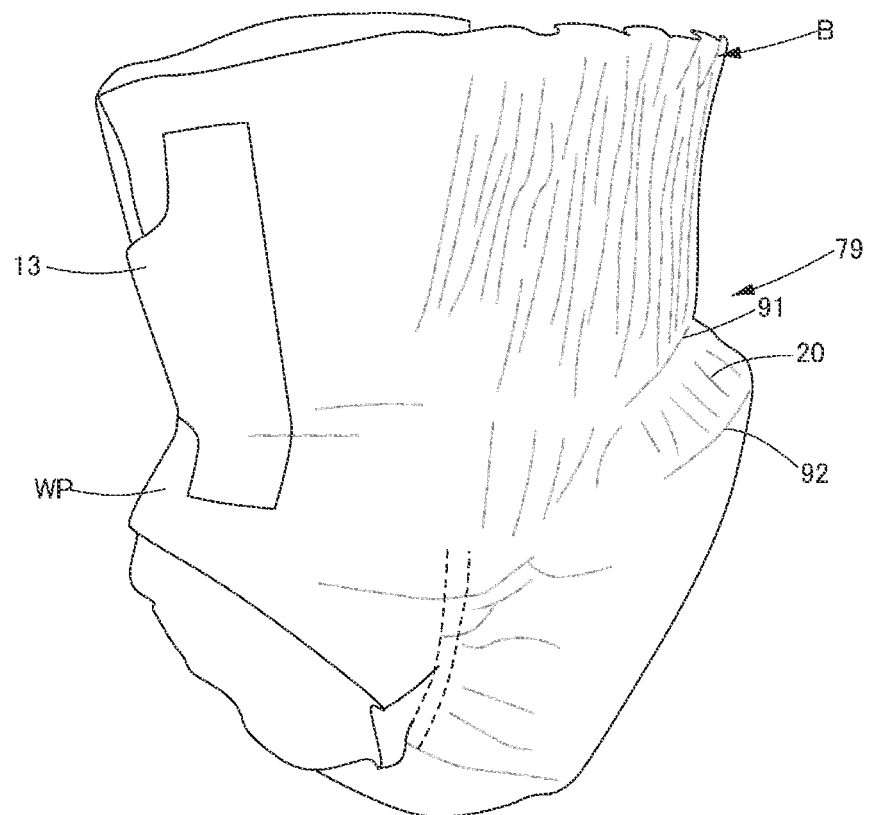

[FIG.20]
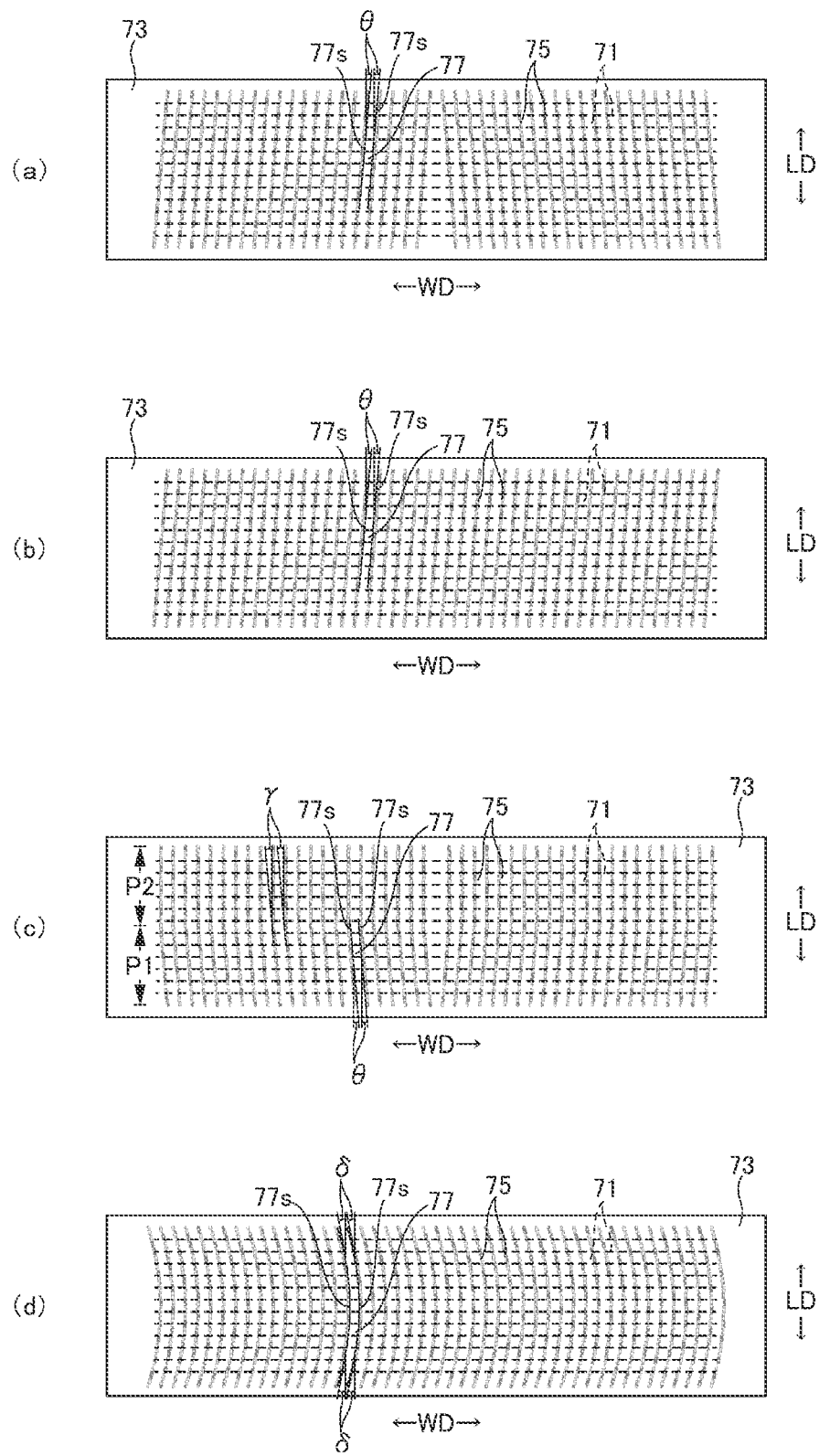

[FIG.21]
(a)
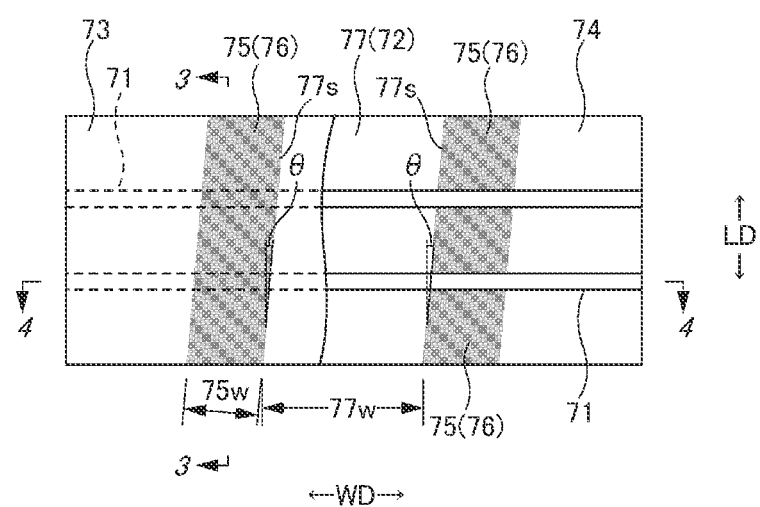
(b)
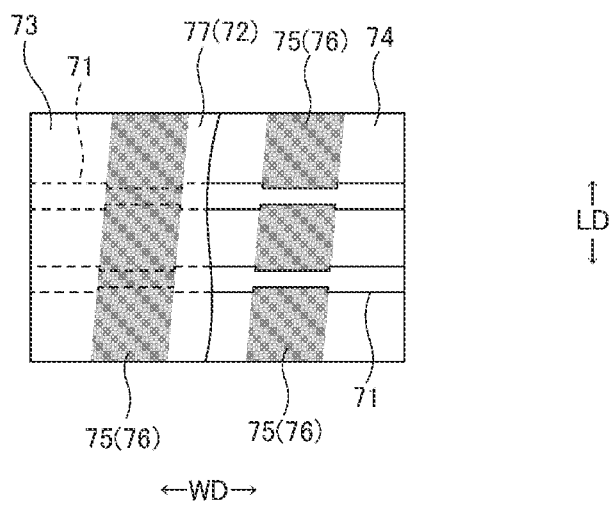

[FIG.22]
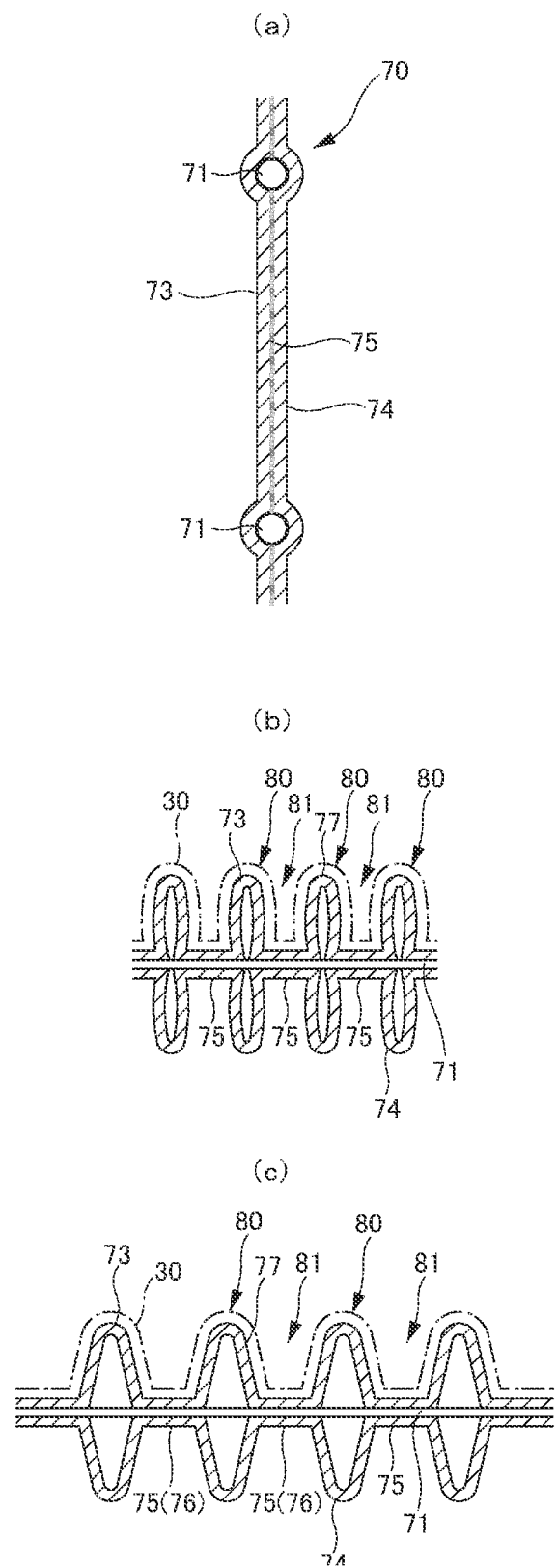

[FIG.23]
(a)
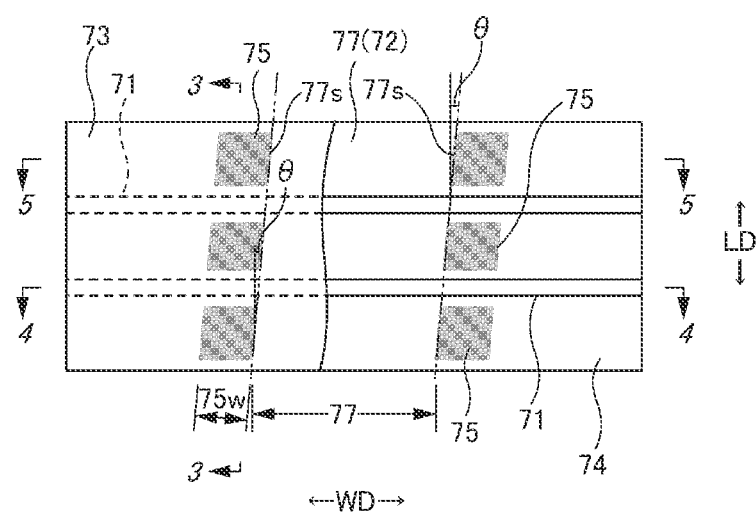
(b)
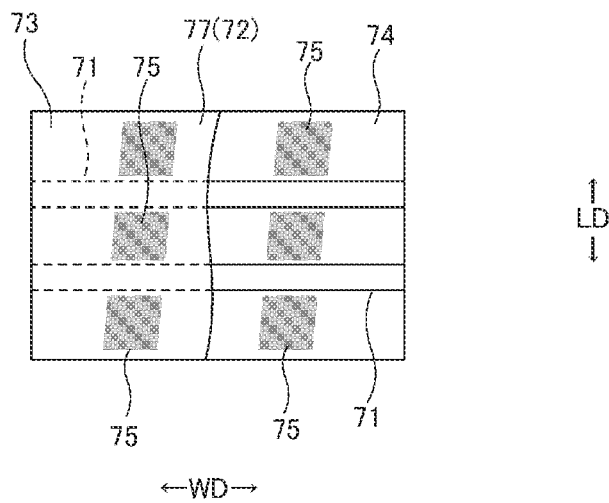

[FIG.24]
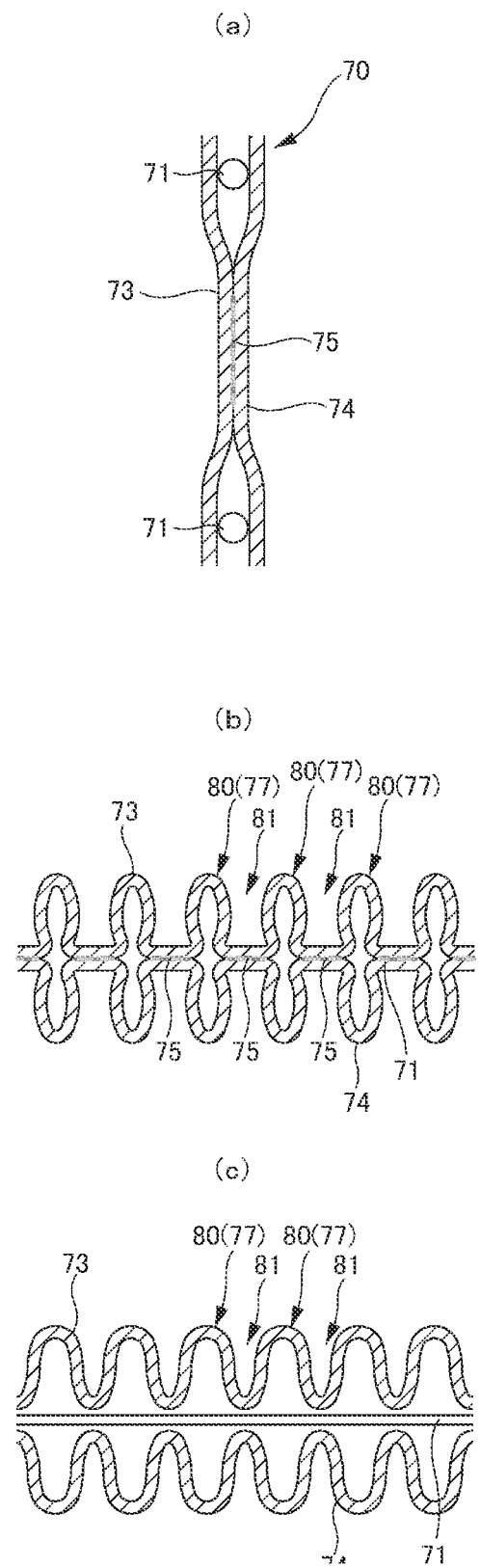

[FIG.25]
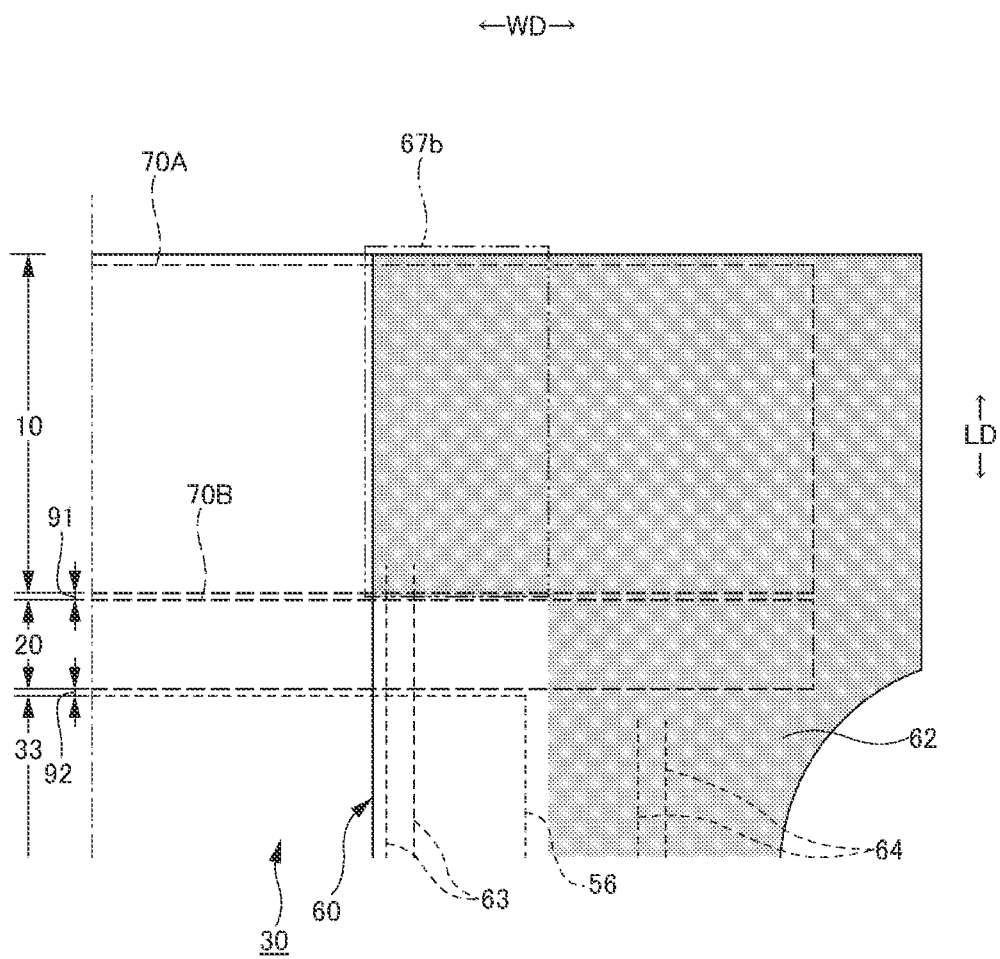

[FIG.26]
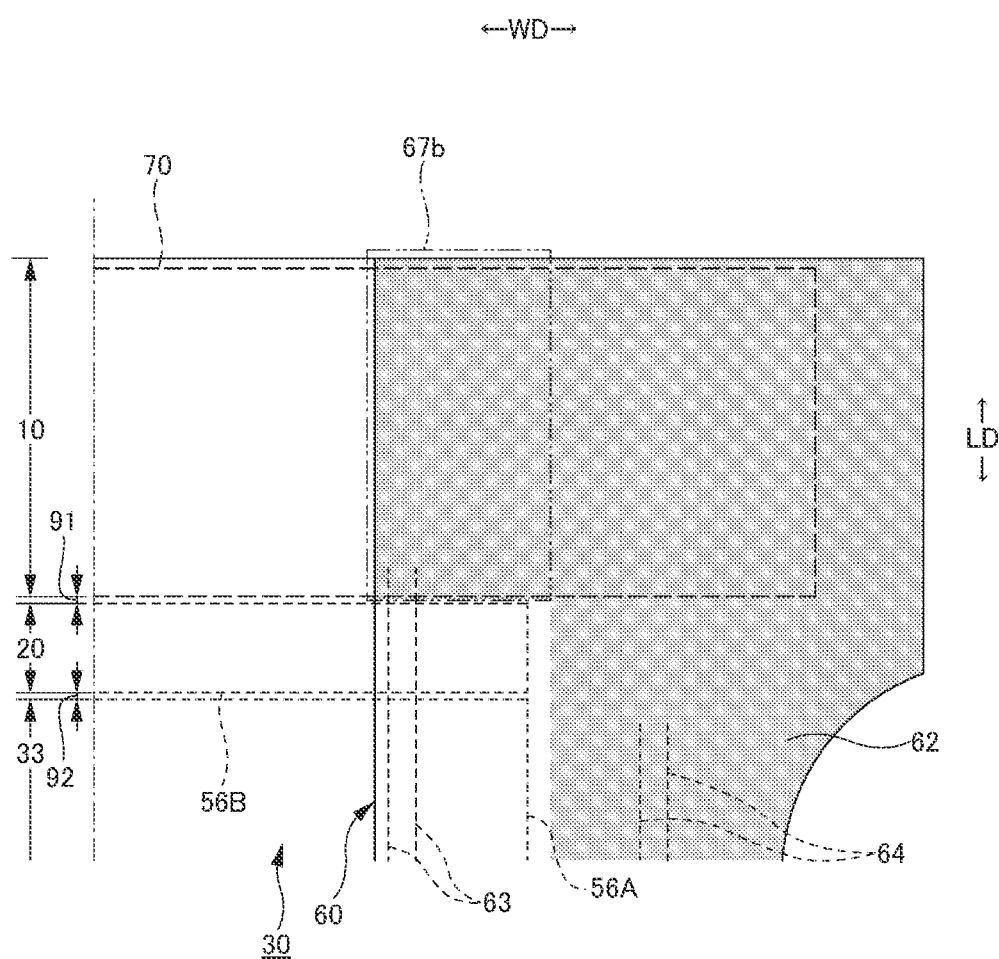

ATTACHABLE-TYPE DISPOSABLE WEARING ARTICLE

CROSS-REFERENCE TO RELATED APPLICATIONS

This application is the U.S. national stage application of International Application PCT/JP2021/009195, filed Mar. 9, 2021, which international application was published on Sep. 30, 2021, as International Publication WO 2021/192999 in the Japanese language. The International Application claims priority of Japanese Patent Application No. 2020-054784, filed Mar. 25, 2020. The international application and Japanese application are both incorporated herein by reference, in entirety.

FIELD OF ART

The present invention relates to attachable-type disposable wearing articles, including tape-type disposable diapers.

BACKGROUND ART

A common attachable-type disposable wearing article has a crotch section containing the middle of the front-back direction, a ventral section extending forward from the middle in the front-back direction, and a dorsal section extending backward from the middle in the front-back direction, and at least the dorsal section has wings extending on opposed lateral sides in the width direction beyond the crotch section. The wings are provided with attaching parts which are to be detachably attached to the exterior surface of the ventral section, while the exterior surface of the ventral section is provided with a target part to which the attaching parts are to be attached. Upon use, the wings are brought onto the exterior face of the ventral section around the lateral sides of the waist to attach the attaching parts of the wings to the target part. Such attachable-type disposable wearing articles are not only for use by babies, but also for use in nursing care (adult use) (see, e.g. Patent Literature 1).

In general, attachable-type disposable wearing articles fit more poorly in the round-waist direction compared to the underpants-type disposable wearing articles. In order to remedy leakage on the back, it is proposed to provide the dorsal section with a waist stretchable region having waist elastic members, and raise a standup region between this waist stretchable region and the absorber body by means of the contracting force of the standup gather parts provided on opposed lateral sides, to thereby define a reservoir space on the crotch side of the waist stretchable region (e.g., see Patent Literature 1).

It is important for the attachable-type disposable wearing articles disclosed in Patent Literature 1 to bend along the back edge of the standup region in order to stably retain the shape and position of the reservoir space, but the bending position may likely be displaced forward to develop an inadvertent folding line in the middle of the front-back direction of the standup region, and the article may disadvantageously tend to bend along this inadvertent folding line.

PRIOR ART LITERATURE

Patent Literature

Patent Literature 1: JP 2001-061888 A

SUMMARY OF THE INVENTION

Problems to be Solved by the Invention

It is therefore a primary object of the present invention to improve retainability of the reservoir space.

Means for Solving the Problem

The attachable-type disposable wearing articles which achieve the above-mentioned object are as follows:
<First Aspect>
An attachable-type disposable wearing article including: a crotch section containing a middle of front-back direction;
  a ventral section extending forward of the middle of the front-back direction;
  a dorsal section extending backward of the middle of the front-back direction;
  an absorber body contained in a region including the crotch section;
  an attaching part provided in each of opposed lateral portions of the dorsal section, and to be detachably attached to an exterior face of the ventral section;
  an end flap extending backward of a back edge of the absorber body;
  a waist elastic member fixed to the end flap; and
  standup gather parts which stand up from a top face along shielding positions of bodily waste on widthwise opposed lateral sides,
  wherein a region containing the waist elastic member is contracted in the width direction together with the waist elastic member, and has a waist stretchable region stretchable in the width direction,
  wherein each of the standup gather parts has a root portion fixed outward in the width direction of a shielding position, a main body portion extending from the root portion, a front laid-down portion and a back laid-down portion formed by fixing a front end portion and a back end portion, respectively, of the main body portion in a laid down state, a standup portion formed by unfixing the main body portion between the front laid-down portion and the back laid-down portion, and a gathering elastic member attached at least to a free edge area of the standup portion,
  wherein at least the free edge area of the standup portion is contracted in the front-back direction together with the gathering elastic member and is stretchable in the front-back direction,
  wherein a linear first bending part extending in the width direction from a front edge of one of the back laid-down portions to a front edge of the other of the back laid-down portions and a linear second bending part extending in the width direction and spaced forwardly apart from the first bending part are provided,
  wherein a first area adjacent backward to the first bending part and a second area between the first bending part and the second bending part are provided,
  wherein the waist stretchable region is provided at least between the opposed right and left back laid-down portions,
  wherein the first bending part has lower rigidity compared to the first area and the second area, and
  wherein, as the standup portions contract, the second area is raised along the second bending part as a stand-up line, and the first area is bent back along the first bending part with respect to the second area.

<Effect>

According to the present attachable-type disposable wearing article, with the contracting force of the gathering elastic members of the standup gather parts, the second area is raised along the second bending part as the stand-up line, while a portion of the waist stretchable region located in the first area is, due to the contraction in the width direction, pressed against the skin of the wearer, so that the first area is bent back along the first bending part with respect to the second area. Accordingly, in the present attachable-type disposable wearing article, the second area is raised, and the first area backward thereof is pressed against the skin of the wearer, which lead to the back edge of the absorber body and its front and back vicinities being depressed almost over the entire width of the absorber body to ensure formation of a deep, wide reservoir space (pocket). On the waist side of the depression forming the reservoir space, the second area is raised and the first area backward thereof is pressed against the skin of the wearer, so that the backward migration of the bodily waste is highly effectively held back, while good fitting against the body surface of a wearer is provided.

Further, the first bending part has lower rigidity and is thus easier to bend compared to the areas forward and backward thereof, so that the bending position of the first bending part is hard to be displaced forward, which facilitates retention of the shape and position of the reservoir space. Even when the bending position is displaced forward of the first bending part by external force temporarily applied during use or product packaging to form a slight inadvertent folding line, the first bending part is still easier to bend, and thus the bending position is returned to the first bending part upon release from the external force to retain the shape and position of the reservoir space.

<Second Aspect>

The attachable-type disposable wearing article according to the first aspect, further including a first sheet layer adjacent to a top side of the waist elastic members, and a second sheet layer adjacent to an underside of the waist elastic members, wherein the waist elastic member is a plurality of elongate waist elastic members each extending in the width direction and arranged at intervals in the front-back direction, wherein the first area and the second area each contain at least one of the waist elastic members, wherein, in the first area and the second area, joined zones of the first sheet layer and the second sheet layer extending backward from a vicinity of the first bending part crossing the waist elastic members and unjoined zones of the first sheet layer and the second sheet layer extending forward from a vicinity of the first bending part crossing the waist elastic members are provided alternately and repeated in the width direction, and wherein the first bending part is free of the joined zones.

<Effect>

With such a structure, the portion containing the joined zones has a relatively higher rigidity, whereas the portion without the joined zones has a relatively lower rigidity. As a result, a first bending part with lower rigidity may be formed with a simple structure using a particular pattern of the joined zones. On the other hand, higher rigidity is imparted to the second area by contraction in the width direction, which further improves the rentainability of the reservoir space.

<Third Aspect>

The attachable-type disposable wearing article according to the second aspect, wherein a stretch rate of the waist elastic members in the spread state is 160 to 230%.

<Effect>

The stretch rate of the waist elastic members may suitably be decided, and is preferably within the above range in view of improved rigidity of the second area.

<Fourth Aspect>

The attachable-type disposable wearing article according to any one of the first to third aspects, further including a stretchable sheet which includes the waist elastic members, and the first and second sheet layers covering a top side and an underside thereof, and is attached to a region including the end flap, wherein the stretchable sheet has, in its front end portion, an edge portion without the waist elastic members, and wherein a front edge of the stretchable sheet extends forward at least to a front edge of the second area.

<Effect>

In this way, with the front edge of the stretchable sheet extending forward at least to the front edge of the second area, the stretchable sheet is present all over the front-back direction of the second area to improve the rigidity. Thus, the second area is securely raised to make the reservoir space hard to collapse.

<Fifth Aspect>

The attachable-type disposable wearing article according to any one of the first to fourth aspects, wherein the second area is exclusive of the absorber body.

<Effect>

According to this aspect, the second area, which is exclusive of the absorber body, has the advantage in that the thickness increases little even when the second area falls toward the crotch side along the second bending part, and it is particularly preferred to combine this aspect with at least one of the second to fourth aspects, since the rigidity of the second area is relatively low.

<Sixth Aspect>

The attachable-type disposable wearing article according to any one of the first to fourth aspects, wherein the absorber body includes a primary absorber body provided in a third area adjacent forward to the second bending part, and an auxiliary absorber body provided in the second area, and wherein a back edge of the auxiliary absorber body is coincident with a back edge of the second area.

<Effect>

According to the present attachable-type disposable wearing article, the second area is securely raised to make the reservoir space hard to collapse, liquid portion of the bodily waste introduced into the reservoir space may be absorbed and held in the auxiliary absorber body in the second area, and the difference in rigidity between the first bending part and the portion forward thereof is particularly large to more securely keep the bending position from displacing.

Effect of the Invention

According to the present invention, advantages, such as improvement in retainability of the reservoir space, is provided.

BRIEF DESCRIPTION OF THE DRAWINGS

FIG. 1 is a plan view of a tape-type disposable diaper in its spread state, illustrating the interior surface thereof.

FIG. 2 is a plan view of the tape-type disposable diaper in its spread state, illustrating the exterior surface thereof.

FIG. 3 is a cross-sectional view taken along lines 6-6 in FIG. 1.

FIG. 4 is a cross-sectional view taken along lines 7-7 in FIG. 1.

FIG. 5 is a sectional view taken along lines 5-5 in FIG. 1.

FIG. 6 is a sectional view taken along lines 9-9 in FIG. 1.

FIG. 7 is an exploded view of a relevant part.

FIG. 8 is a plan view of a relevant part, shown enlarged, on one side of the center line (dash-dot line) passing the center of the width (the other side appears symmetric with respect to the center line).

FIG. 9(a) is a sectional view taken along lines 8-8 in FIG. 1, and FIG. 9(b) is a sectional view schematically illustrating the raised state thereof.

FIG. 10 is a plan view of a relevant part, shown enlarged, on one side of the center line (dash-dot line) passing the center of the width (the other side appears symmetric with respect to the center line).

FIG. 11 is a plan view of a relevant part, shown enlarged, on one side of the center line (dash-dot line) passing the center of the width (the other side appears symmetric with respect to the center line).

FIG. 12 is an exploded view of a relevant part.

FIG. 13 is a plan view of a relevant part, shown enlarged, on one side of the center line (dash-dot line) passing the center of the width (the other side appears symmetric with respect to the center line).

FIG. 14(a) is a sectional view corresponding to the sectional view taken along lines 8-8 in FIG. 1, and FIG. 14(b) is a sectional view schematically illustrating the raised state thereof.

FIG. 15(a) is a sectional view corresponding to the sectional view taken along lines 8-8 in FIG. 1, illustrating the reservoir space in the collapsed state, and FIG. 15(b) is a sectional view thereof taken along lines 9-9.

FIG. 16 is an exploded view of a relevant part.

FIG. 17 is a plan view of a relevant part, shown enlarged, on one side of the center line (dash-dot line) passing the center of the width (the other side appears symmetric with respect to the center line).

FIG. 18 is a front view of a relevant part of a sample in the natural length.

FIG. 19 is a side view of a sample in the worn state.

FIG. 20 illustrates plan views of the stretchable sheet.

FIG. 21 shows relevant part of the stretchable sheet, wherein FIG. 21(a) is a plan view in the spread state, and FIG. 21(b) is a plan view in the natural length.

FIG. 22(a) is a sectional view taken along lines 3-3 in FIG. 21, FIG. 22(b) is a sectional view in the natural length taken along lines 4-4 of FIG. 21, and FIG. 21(c) is a sectional view in a stretched state to some extent taken along lines 4-4 of FIG. 21.

FIG. 23 shows relevant part of the stretchable sheet, wherein FIG. 23(a) is a plan view in the spread state, and FIG. 23(b) is a plan view in the natural length.

FIG. 24(a) is a sectional view taken along lines 3-3 in FIG. 23, FIG. 24(b) is a sectional view in the natural length taken along lines 5-5 of FIG. 23, and FIG. 24(c) is a sectional view in a stretched state to some extent taken along lines 4-4 in FIG. 23.

FIG. 25 is a plan view of a relevant part, shown enlarged, on one side of the center line (dash-dot line) passing the center of the width (the other side appears symmetric with respect to the center line).

FIG. 26 is a plan view of a relevant part, shown enlarged, on one side of the center line (dash-dot line) passing the center of the width (the other side appears symmetric with respect to the center line).

EMBODIMENTS FOR CARRYING OUT THE INVENTION

FIGS. 1 to 9 show an example of a tape-type disposable diaper, wherein reference sign X refers to the overall width of the diaper exclusive of the attaching tapes, reference sign L refers to the overall length of the diaper and, in the sectional views, dotted pattern regions represent a hot melt adhesive as joining means for joining various components located on top or bottom side thereof. The hot melt adhesive may be applied using a known technique, such as slot application, bead application in continuous lines or dotted lines, spray application in spiral or Z shapes, or pattern coating (transfer of a hot melt adhesive by relief printing). In place of or in addition to these, fixing portions of elastic members may be fixed to adjacent members by application of a hot melt adhesive to the external surface of the elastic members. Examples of the hot melt adhesive include, but not limited to, EVA-based, pressure-sensitive rubber-based (elastomer-based), polyolefin-based, and polyester/polyamide-based adhesives. The joining means for joining various components may alternatively be material melt-bonding, such as heat sealing or ultrasonic sealing.

This tape-type disposable diaper has a crotch section containing the middle of the front-back direction LD, a ventral section F extending forward of the middle of the front-back direction LD, and a dorsal section B extending backward of the middle of the front-back direction LD. Further, this tape-type disposable diaper has an absorber body 56 contained in the region including the crotch section, a liquid-pervious top sheet 30 covering the top side of the absorber body 56, a liquid-impervious sheet 11 covering the underside of the absorber body 56, and an exterior nonwoven sheet 12 covering the underside of the liquid-impervious sheet to constitute the product exterior surface.

Materials and features of each part will now be explained in turn.

<Absorber Body>

The absorber body 56 may be in a rectangular shape as in the illustrated embodiment, or a shape having a middle portion in the front-back direction narrowed so as to fit around each leg (hourglass-like shape). Reference sign 56x refers to the overall width of the absorber body 56. The absorber body 56 absorbs and holds excreted fluid, and may be formed of an assembly of fibers. Such an assembly of fibers may be a stack of discontinuous fibers of fluff pulp, synthetic fibers, or the like, as well as an assembly of filaments obtained by opening, where necessary, tows (fiber bundles) of synthetic fibers, such as cellulose acetate. The basis weight of the fibers may be about 100 to 300 g/m$^2$ for a stack of fluff pulp or discontinuous fibers, and about 30 to 120 g/m$^2$ for an assembly of filaments. The fineness of the synthetic fibers, when used, is, for example, 1 to 16 dtex, preferably 1 to 10 dtex, more preferably 1 to 5 dtex. The filaments in the assembly may be uncrimped fibers, but may preferably be crimped fibers.

The bending resistance of the absorber body 56 is not particularly limited, and may be 75 mm or more as measured in the front-back direction of the absorber body 56 in accordance with JIS L 1913: 2010 "41.5° Cantilever Method" for better raising of the second area 20 be discussed later.

<Superabsorbent Polymer Particles>

The absorber body 56 may be caused partially or entirely to contain superabsorbent polymer particles. The superabsorbent polymer particles include not only "particles", but also "powders". Superabsorbent polymer particles used in this kind of attachable-type disposable wearing articles may be used as they are as the superabsorbent polymer particles here. The particle size of the superabsorbent polymer particles is not particularly limited and, for example, the particles may preferably have such a particle size that, when the particles are subjected to sieving (five-minute shaking) through a 500 μm standard sieve (JIS Z8801-1: 2006), followed by further sieving (five-minute shaking) through a 180 μm standard sieve (JIS Z8801-1: 2006) of the particles sieved through the previous sieve, the percentage of the particles remaining on the 500 μm standard sieve is 30 wt % or less and the percentage of the particles remaining on the 180 μm standard sieve is 60 wt % or more.

Any materials of the superabsorbent polymer particles may be used without particular limitation, and those having a water absorption of 40 g/g or more are preferred. The superabsorbent polymer particles may be starch-based, cellulose-based, or synthetic polymer-based, and starch-acrylic acid (salt) graft copolymers, saponified products of starch-acrylonitrile copolymers, cross-linked sodium carboxymethyl cellulose, or acrylic acid (salt) polymers may be used. The superabsorbent polymer particles may preferably be in ordinary powder or granular form, but particles in other forms may also be used.

The superabsorbent polymer particles having a water absorption speed of 70 seconds or less, particularly 40 seconds or less, may preferably be used. With too slow a water absorption speed, the absorber body 56 is likely to undergo so-called back flow, wherein liquid supplied into the absorber body 56 returns out of the absorber body 56.

The superabsorbent polymer particles may preferably be those having a gel strength of 1000 Pa or higher. With such property, when the superabsorbent polymer particles are formed into a bulky absorber body 56, stickiness after liquid absorption may effectively be limited.

The basis weight of the superabsorbent polymer particles may suitably be decided depending on the absorption amount required in a use of the absorber body 56. Thus, it depends, but the basis weight may usually be 50 to 350 g/m².

<Packing Sheet>

For limiting escape of the superabsorbent polymer particles, or for improving maintenance of the shape of the absorber body 56, the absorber body 56 may be wrapped with a packing sheet 58 to produce an absorbent element 50, which is to be disposed inside. The packing sheet 58 may be tissues, in particular, crepe paper, nonwoven fabric, polyethylene-laminated nonwoven fabric, perforated sheet, or the like, provided that sheets through which the superabsorbent polymer particles will not escape are preferred. When nonwoven fabric is used in place of crepe paper, hydrophilic SMMS (spunbonded/melt-blown/melt-blown/spunbonded) nonwoven fabric is particularly preferred, which may be made of polypropylene, polyethylene/polypropylene, or the like. The basis weight is preferably 5 to 40 g/m², particularly 10 to 30 g/m².

One such packing sheet 58 may be used, as shown in FIG. 3, to wrap the entire absorber body 56, or a plurality of sheets, such as an upper sheet and a lower sheet, may be used to wrap the entire absorber body 56. Alternatively, the packing sheet 58 may be omitted.

<Top Sheet>

The top sheet 30 is liquid-pervious, and may be, for example, perforated or imperforated nonwoven fabric or porous plastic sheet.

The top sheet 30 extends in the front-back direction LD from the front end to the back end of the product, and in the width direction WD laterally beyond the absorber body 56, but its shape may suitably be modified, for example, so that the width of the top sheet 30 is shorter than the entire width of the absorber body 56, in case, for example, where the starting points of standup gather parts 60 to be discussed later are located on the center side of the side edges of the absorber body 56 in the width direction WD, or otherwise required.

<Intermediate Sheet>

For the purpose of preventing back flow of the liquid permeated through the top sheet 30, an intermediate sheet (also referred to as "second sheet") 40 may be provided on the underside of the top sheet 30. The intermediate sheet 40 may alternatively be omitted.

The intermediate sheet 40 may preferably be selected from various types of nonwoven fabric, and may preferably be of air-through nonwoven fabric for its bulkiness. The air-through nonwoven fabric is preferably made of composite fibers of a core-clad structure, wherein the resin for the core may be polypropylene (PP), or preferably polyester (PET), which has a higher stiffness. The basis weight is preferably 17 to 80 g/m², more preferably 25 to 60 g/m². The fineness of the raw material fibers of the nonwoven fabric is preferably 2.0 to 10 dtex. For making nonwoven fabric bulky, it is also preferred to use eccentric fibers having off-centered cores, hollow fibers, or eccentric hollow fibers, entirely as the raw material fibers or partially mixed fibers.

In the illustrated embodiment, the intermediate sheet 40 is shorter than the absorber body 56 in width and is arranged in the center, but may be provided over the entire width. Further, the intermediate sheet 40 may be provided over the entire length of the diaper, or only in the middle portion including the excretion area, as in the illustrated embodiment.

<Liquid-Impervious Sheet>

The liquid-impervious sheet 11 is not particularly limited, and may preferably have moisture-permeability. As the liquid-impervious sheet 11, for example, a microporous sheet may preferably be used which is obtained by kneading an inorganic filler in a polyolefin-based resin, such as polyethylene or polypropylene, molding the resulting mixture into a sheet, and then uni- or biaxially drawing the sheet. Alternatively, the liquid-impervious sheet 11 may be those based on nonwoven fabric with improved waterproof property.

The liquid-impervious sheet 11 preferably extends over the same or wider extent than that of the absorber body 56 in the front-back direction LD and in the width direction WD but, when another liquid-shielding means is present, may not cover the ends or edges of the absorber body 56 in the front-back direction LD and in the width direction WD, as necessary.

<Exterior Nonwoven Sheet>

The exterior nonwoven sheet 12 covers the entire underside of the liquid-impervious sheet 11 to impart a fabric-like appearance to the product exterior. One sheet of nonwoven fabric may be used, or a plurality of sheets of nonwoven fabric may be stacked and used. In the latter case, the nonwoven sheets may preferably be adhered together with a hot melt adhesive or the like. The nonwoven sheet, when used, preferably has a fineness of its constituting fibers of 1.6 to 2.3 dtex, a basis weight of 15 to 25 g/m², and a thickness of 0.3 to 0.8 mm.

<Standup Gather Parts>

It is preferred to provide standup gather parts 60 which stand up from the top face along the shielding positions of bodily waste on widthwise WD opposed lateral sides of the top face for blocking the bodily waste migrating laterally on the top sheet 30 and thereby preventing so-called side leakage.

More specifically, each of the standup gather parts 60 has a root portion 65 fixed to the region including a side flap SF, a main body portion 66 extending from the root portion, a front laid-down portion 67f and a back laid-down portion 67b formed by fixing the front and back end portions, respectively, of the main body portion 66 in a laid down state, and a standup portion 68 formed by unfixing the main body portion 66 between the front laid-down portion 67f and the back laid-down portion 67b. The standup portion 68 has gathering elastic members 63 attached at least to its free edge area.

The standup gather parts 60 in the illustrated embodiment are each composed of a gathered sheet 62, which is folded in double to form the free edge of the main body portion 66 (the edge opposite from the root portion 65) so that the area including the free portion has a double-layered structure. The gathering elastic members 63 are held between the layers of this double-layered structure. The gathering elastic members 63 may be provided only in the standup portion 68, or may preferably be fixed, as in the illustrated embodiment, from the back end area of the front laid-down portion 67f to the front end area of the back laid-down portion 67b, so that the contracting force of the gathering elastic members 63 not only acts over the entire standup portion 68, but also on the end areas of the front laid-down portion 67f and of the back laid-down portion 67b.

The inner face of the gathered sheet 62 has a joining start edge positioned on a lateral side portion of the top sheet 30 in the width direction WD, and the portion outward in the width direction of this joining start edge is bonded to the inner face of the corresponding side flap SF, i.e., in the illustrated embodiment, to a lateral side portion of the liquid-impervious sheet 11 and to a lateral side portion of the exterior nonwoven sheet 12 located laterally outward thereof in the width direction, with a hot melt adhesive or the like.

Each standup gather part 60 is fixed to the top sheet 30 on the inner side in the width direction of the joining start edge at both end portions in the product front-back direction, while the standup portion 68 between the end portions of the standup gather part 60 is a non-fixed free portion. Accordingly, with the contracting force of the gathering elastic members 63, the standup portion 68 is contracted in the front-back direction and raised while it is stretchable in the front-back direction, so as to be brought into close contact with the body surface. Further, the standup portion 68, while contracting in the front-back direction under the contracting force of the gathering elastic members 63, deforms to bring the front laid-down portion 67f and the back laid-down portion 67b closer.

Though not shown, as is well known, the main body portion 66 of the standup gather part 60 may be formed in double, having a proximal portion extending from lateral outer side to lateral inner side in the width direction, and a distal portion folded toward the body along and extending laterally outward in the width direction from the edge of the proximal portion located closer to the center of the width, and the main body portion 66 may be fixed at both end portions in the front-back direction to form laid-down portions.

The type of the gathered sheet 62 is not particularly limited, and is usually water-repelling for ensuring liquid-shielding property. In particular, for imparting both texture and liquid-shielding property, nonwoven fabric having at least one melt-blown layer between spunbonded layers (SMS nonwoven fabric, SMMS nonwoven fabric, SSMS nonwoven fabric, or SSMMS nonwoven fabric) is preferred. One sheet of nonwoven fabric may be used, or a plurality of sheets of nonwoven fabric may be stacked and used. In the latter case, the nonwoven sheets may preferably be adhered together with a hot melt adhesive or the like.

The gathering elastic members 63 may be rubber threads (spandex rubber threads having a fineness of about 420 to 1120 dtex) or the like. A plurality of gathering elastic members 63 may be provided on each side of the product as shown in FIGS. 1 and 2, or one gathering elastic member 63 may be provided on each side. The stretch rate of the gathering elastic members 63 in the spread state may suitably be decided, and may be, for example, about 230 to 270%.

<Side Flaps>

The tape-type disposable diaper of the illustrated embodiment has a pair of side flaps SF a of the absorber body 56, extending respectively laterally beyond the opposed lateral edges of the absorber body 56. The side flaps SF may be formed of the material continuous from the region containing the absorber body 56 (exterior nonwoven sheet 12 or the like), or may be formed of another material and attached.

<Planar Gathers>

Each side flap SF is provided with side elastic members 64, which are of elongate elastic members, such as rubber threads, and are fixed in their stretched state in the front-back direction LD, to thereby form the round-leg portion of each side flap SF into planar gathers. The side elastic members 64 may be provided between the gathered sheet 62 and the liquid-impervious sheet 11 in the outer vicinity in the width direction of the joining start edge in the joined portion of the gathered sheet 62 as in the illustrated embodiment, or between the liquid-impervious sheet 11 and the exterior nonwoven sheet 12 in each side flap SF. A plurality of the side elastic members 64 may be provided on each lateral side as in the illustrated embodiment, or only one side elastic member 64 may be provided on each lateral side.

The planar gathers are formed where the contracting force of the side elastic members 64 acts (in the illustrated embodiment, where the side elastic members 64 are shown). Thus, structures are conceivable, wherein the side elastic members 64 are present only in the area of the planar gathers, or wherein the side elastic members 64 are present on either or both of the front side and back side of the planar gathers, but the contacting force of the side elastic members 64 acts only in the area of the planar gathers, while the contracting force is made not to act in the area other than the area of the planar gathers (substantially equivalent to absence of the elastic members) by finely cutting the side elastic members at one or a plurality of locations other than the area of the planar gathers, by not fixing the side elastic members 64 to the sheets between which the side elastic members 64 are interposed, or by both.

<Wings>

In the present tape-type disposable diaper, the dorsal section B is provided with wings WP extending beyond the crotch section M in the width direction WD. Similarly, the ventral section F is also provided with wings WP extending beyond the crotch section M in the width direction WD. These wings WP may be formed of parts separate from the remaining portions. However, in the structure having the side flaps SF as in the illustrated embodiment, it is preferred for facilitating production that the wings WP are formed by cutting out each lateral side of the side flap SF in the middle in the front-back direction LD to form a concave edge extending from the lateral edge of the crotch section M to the lower edge of each wing.

<Attaching Tapes>

Each wing WP in the dorsal section B is provided with an attaching tape 13 as shown in FIGS. 1, 2, and 5, which is to be detachably attached to the exterior face of the ventral section F. In fitting the diaper, the attaching tapes 13 are brought onto the exterior face of the ventral section F around the lateral sides of the waist to attach the attaching parts 13A of the attaching tapes 13 to the appropriate positions on the exterior face of the ventral section F.

Each attaching tape 13 has, as shown in FIG. 5, a base sheet 13S forming a base portion 13C fixed to the wing WP and a body portion 13B extending from the base portion 13C, and an attaching part 13A disposed in the middle of the body portion 13B in the width direction WD in the base sheet 13S and is to be attached to the ventral section F. In the body portion 13B, the area closer to the base portion 13C than the attaching part 13A is a non-attachable area, which is not to be attached to the ventral section F, whereas the area opposite to the non-attachable area forms a grip area. These non-attachable area and the grip area are formed only of the base sheet 13S constituting the body portion 13B.

The attaching part 13A is formed of a hook member (male part) of a mechanical fastener (hook and loop fastener). The hook member has a number of engaging projections on its connecting surface, and the engaging projections may be in various shapes, such as (A) tick-shaped, (B) J-shaped, (C) mushroom-shaped, (D) T-shaped, or (E) double J-shaped (wherein J-shaped parts are joined back to back), and any shape may be employed.

Further, the base sheet 13S forming from the base portion 13C to the body portion 13B may be formed of nonwoven fabric, plastic film, polyethylene-laminated nonwoven fabric, paper, or composites thereof.

Each attaching part 13A in the illustrated embodiment is provided on the base sheet 13S of the attaching tape 13 extending from the wing WP, but may be provided directly on the wing WP.

<Target Sheet>

At the sites in the ventral section F to be engaged by the attaching tapes 13, a target sheet 12T is disposed.

The material of the target sheet 12T is not particularly limited and, when the attaching parts A are the hook members, the target sheet 12T may be formed of a continuous fiber nonwoven fabric wherein the fibers are melt-bonded together locally through intermittent ultrasonic sealing. In this case, the continuous fiber nonwoven fabric preferably has a fineness of its constituent fibers of 5 to 10 dtex, a basis weight of 25 to 40 g/m² and a thickness of 0.3 to 0.8 mm.

When the attaching parts 13A are the hook members, the target sheet 12T may have a multitude of thread loops on which the engaging projections of the hook members are caught, provided on the surface of a substrate made of plastic film or nonwoven fabric. A specific example of the above may be a composite sheet material wherein a substrate is stitched with looped pile fiber yarns at least on its exterior face. In such a sheet material, on the exterior face of the substrate, i.e., the exterior face of the disposable diaper, the looped pile fiber yarns are projected at intervals in the latitudinal and longitudinal directions, whereas on the back side (on the side of the wearer) of the substrate, the pile fiber yarns are combined with each other to form a matrix of the pile fiber radial threads.

Further, when the attaching parts 13A are the hook members and the attaching sites of the attaching tapes 13 in the ventral section F are formed of nonwoven fabric (e.g., having exterior nonwoven sheet 12 as in the illustrate embodiment), a target sheet 12T may be disposed inside the exterior nonwoven fabric 12, which sheet is made of plastic sheet, paper, nonwoven fabric, or the like, having attaching positions, such as a scale, displayed by printing thereon. In this case, the user may effect the attachment by engaging the hook members of the attaching parts 13A with the fibers of the exterior nonwoven sheet 12 at the positions on the target sheet 12T seen through the exterior nonwoven sheet 12.

On the other hand, when the attaching parts 13A are in the form of a pressure-sensitive adhesive layer, the target sheet 12T may be made of plastic film with a smooth surface for good adhesion, which has been subjected to release lining.

<End Flaps>

The tape-type disposable diaper of the present invention has a pair of end flaps EF exclusive of the absorber body 56, extending respectively on the front and back sides of the absorber body 56. The materials constituting the end flaps EF vary depending on the structure of the diaper. For example, an end flap EF may be formed from parts of the top sheet 30, the intermediate sheet 40, the gathered sheet 62, the liquid-impervious sheet 11, and the exterior nonwoven fabric 12 which extend forward and backward of the absorber body 56, are stacked on one another, and joined together. When the intermediate sheet 40 or the exterior nonwoven sheet 12 is eliminated unlike the illustrated embodiment, the end flaps EF are formed with the top sheet 30 and the liquid-impervious sheet 11. Alternatively, a separate sheet for forming an end flap EF may be fixedly added forward of or backward of the absorber body 56 to form an end flap EF.

The dimension in the front-back direction LD of the end flap EF in the dorsal section B is preferably larger than the dimension in the front-back direction LD of the base portions 13C of the attaching tapes 13. Usually, the dimension in the front-back direction LD of the end flap EF is preferably about 20 to 25% of the dimension L in the front-back direction LD of the overall diaper, and is suitably about 80 to 120 mm for baby diapers.

<Waist Elastic Members>

As shown in FIGS. 7 to 9 as well as in FIGS. 20(a), 21, and 22, waist elastic members 71 are fixed to the end flap EF. In the region containing the waist elastic members 71, a waist stretchable region 79 is formed which is stretchable in the width direction WD, and contracts in the width direction WD as the waist elastic members 71 contract to form ridges 80 on its top face as shown in FIGS. 15, 18, or the like. The region containing the waist elastic members 71 may entirely or partially be the waist stretchable region 79. That is, in the region containing the waist elastic members 71, elasticity of part of the waist elastic members 71 (e.g., in the opposed ends as shown in FIG. 20) may be wrecked by common technique, such as cutting. As may be noted from the above, the waist stretchable region 79 is a region bounded by the lines circumscribing the area in which the elasticity of none of the waist elastic members 71 is wrecked.

The wait elastic members 71 are not particularly limited as long as they are made of a material which per se elastically stretches and contracts. For example, elongate elastic materials, such as those in the form of threads or strings (e.g., spandex rubber thread having a fineness of about 420 to 1120 dtex), elastic materials in the form of a web or perforated or imperforated film, or stretchable nonwoven fabric may suitably be used.

When elongate elastic members are used as the waist elastic members 71, it is preferred to provide a plurality of elongate waist elastic members 71 each extending in the width direction WD and arranged at intervals in the front-back direction LD, a first sheet layer 73 adjacent to the top side of the waist elastic members 71, and a second sheet layer 74 adjacent to the underside of the waist elastic members 71, as in the illustrated embodiment.

The first sheet layer 73 and the second sheet layer 74 are not particularly limited and, for example, other members constituting the end flap EF (e.g., top sheet 30 and the liquid-impervious sheet 11) may also be used as the first sheet layer 73 and the second sheet layer 74, or a separate first sheet layer 73 and a separate second sheet layer 74 may be provided as in the illustrated embodiment. That is, in the illustrated embodiment, a stretchable sheet 70 wherein the waist elastic members 71 are fixed between a separate first sheet layer 73 and a separate second sheet layer 74 is attached to the end flap EF. Such a separate first sheet layer 73 and the second sheet layer 74 may be made of various nonwoven fabric.

The first sheet layer 73 and the second sheet layer 74 may be two separate sheets as shown in FIG. 9, or may be one half and the other half of one sheet folded in half along a folding line as shown in FIG. 15.

As the elastic members 71, about five to fifteen elastic members may be disposed at 3 to 10 mm intervals in the front-back direction LD. It is preferred, as in the illustrated embodiment, that the position of the front edge of the waist stretchable region 79 (the front-most waist elastic member 71) is spaced apart in the front-back direction LD from the position of the back edge of the absorber body 56, the front end portion of the absorber body 56 will not contract in the width direction WD, which is preferable. The stretch rate of the elastic members in the spread state may be about 160 to The first sheet layer 73 and the second sheet layer 74 may be joined continuously over both the front-back direction LD and the width direction WD, or joined intermittently at least in one of the directions. Further, it suffices that fixing portions 76 wherein the elastic members 71 are fixed to the first sheet layer 73 and to the second sheet layer 74 are provided at least in the opposed end portions of the waist elastic members 71.

As in the illustrated embodiment, it is preferred that joined zones 75 of the first sheet layer 73 and the second sheet layer 74 provided linearly continuously or intermittently from forward of the waist stretchable region 79 to backward thereof and unjoined zones 77 of the first sheet layer 73 and the second sheet layer 74 provided linearly continuously from forward of the waist stretchable region 79 to backward thereof are arranged alternately and repeatedly in the width direction WD. In this way, when the waist stretchable region 79 is in the contracted state, the first sheet layer 73 and the second sheet layer 74 in the unjoined zones 77 bulge in opposite directions as shown in FIGS. 22(b), 22(c), 24(b), and 24(c), which results in formation of ridges 80 extending continuously from forward of the waist stretchable region 79 to backward thereof and repeated in the width direction WD. Each joined zone 75 may be provided intermittently in the direction transverse to the width direction WD as shown, for example, in FIGS. 23 and 24, but may preferably be provided linearly continuously in the direction transverse to the width direction WD, except for the first bending part to be discussed later as shown in FIGS. 20 to 22.

The width 75w of each joined zone 75 (the dimension in the direction transverse to the locus (tangent line in case of a curved line) of the points located equidistant from the opposed edges of a joined zone 75) preferably does not vary (being constant), but may vary. When the width 75w of the joined zone 75 varies, the maximum width is preferably two to five times the minimum width. The width 75w of the joined zone 75 may suitably be decided, and is usually preferably 0.5 to 2 mm, as the air permeability is poor with too large a width, whereas with too small a width, the joined zones 75 may be separated to deteriorate the stretchability and thus the leak protection property. The dimension 77w in the width direction WD of each unjoined zone 77 in the spread state determines the height of a ridge 80 and is usually preferably 4 to 8 mm.

The fixing portions 76 for the waist elastic members 71 is not particularly limited as long as the first sheet layer 73 and the second sheet layer 74 contract together with the waist elastic members 71 to form the waist stretchable region 79. For example, with the joined zones 75 extending continuously in the direction crossing the waist elastic members 71 as in the embodiment illustrated in FIGS. 21 and 22, each joined zone 75 intersecting with the waist elastic members 71 may act also as a fixing portion 76. On the other hand, when the waist elastic members 71 and the joined zones 75 do not intersect as shown in FIGS. 23 and 24, fixing portions 76 (not shown) may be provided only in the opposed edge portions of the waist stretchable region 79, separate from the joined zones 75.

The joining between the first sheet layer 73 and the second sheet layer 74 in the joined zones 75, and the fixing of the waist elastic members 71 in the fixing portions 76 may be effected with a hot melt adhesive or known means including melt-bonding, such as heat sealing or ultrasonic sealing. In the joined zones 75, the first sheet layer 73 and the second sheet layer 74 may be joined directly where the elastic members are not present, or may be joined indirectly with the waist elastic members 71 interposed.

The stretchable sheet 70 may be, as in the embodiment illustrated in FIGS. 7 to 9(a), interposed between any suitable members placed between the top sheet 30 and the exterior nonwoven sheet 12 (in the illustrated embodiment, interposed between the top sheet 30 and the intermediate sheet 40 on one side and the liquid-impervious sheet 11 on the other side, but may be interposed between the liquid-impervious sheet 11 and the exterior nonwoven sheet 12), or may be disposed as the top-most layer to be located closest to the skin as in the embodiment illustrated in FIGS. 12 to 15 and 16 to 17. In case of the latter, the stretchable sheet 70 may be arranged above the gathered sheet 62 where present (i.e., the entire stretchable sheet is the top-most layer), or may be arranged between the top sheet 30 and the gathered sheet 62.

The joining pattern between the stretchable sheet 70 and the constituent members of the end flap EF stacked with the stretchable sheet 70 is preferably such that ridges 80 similar to the ridges formed in the stretchable sheet 70 are formed in the top face of the waist stretchable region 79. For example, the stretchable sheet 70 and the members of the end flap EF stacked therewith may be joined continuously both in the front-back direction LD and the width direction WD, or joined continuously at least in one of the front-back direction LD and the width direction WD. When the joining between the stretchable sheet 70 and the members of the end flap EF stacked therewith (top sheet 30 or the like) is continuous in the width direction WD, the ridges 80 formed in the stretchable sheet 70 correspond to the ridges 80 formed in the top face of the waist stretchable region 79 as shown in a dash-dot line in FIG. 22(c).

<Reservoir Space>

It is preferred that, as shown enlarged in FIG. 8, a linear first bending part 91 extending in the width direction WD from the front edge of one of the back laid-down portions 67b to the front edge of the other of the back laid-down portions 67b and a linear second bending part 92 extending in the width direction WD and spaced forwardly apart from the first bending part 91 are provided, and a first area 10, which is an area adjacent backward to the first bending part 91, and a second area 20, which is an area located between the first bending part 19 and the second bending part 92, are defined, and the waist stretchable region 79 is provided at least between the opposed right and left back laid-down portions 67b.

In this case, with the contracting force of the gathering elastic members 63 of the standup gather parts 60, the second area 20 is raised along the second bending part as the stand-up line, while a portion of the waist stretchable region 79 located in the first area 10 is, due to the contraction in the width direction WD, pressed against the skin of the wearer, so that the first area 10 is bent back along the first bending part with respect to the second area 20, as shown in FIG. 9(b). Accordingly, in the present attachable-type disposable wearing article, the second area 20 is raised as shown in FIGS. 18 and 19, and the first area 10 backward thereof is pressed against the skin of the wearer, which lead to the back edge of the absorber body 56 and its front and back vicinities being depressed almost over the entire width of the absorber body 56 to ensure formation of a deep, wide reservoir space 21 (pocket). On the waist side of the depression forming the reservoir space 21, the second area 20 is raised and the first area 10 backward thereof is pressed against the skin of the wearer, so that the backward migration of the bodily waste is highly effectively held back, while good fitting against the body surface of a wearer is provided.

It suffices that the waist stretchable region 79 is provided only in the first area 10, as long as the waist stretchable region 79 is formed at least between the right and left back laid-down portions 67b in the first area 10, but preferably provided over the first area 10 and the second area 20. This arrangement includes the embodiment wherein, as in the illustrated embodiment, the waist elastic members 71 are separately provided in the first area 10 and in the second area 20, and an embodiment, not shown, wherein an elastic material in the form of a sheet is provided over the first area 10 and the second area 20.

When the front edges of the back laid-down portions 67b (the position of the first bending part 91) are located forward of the front edge of the waist stretchable region 79, the back laid-down portion 67b, which has a poorer fitting property against the skin, extends forwardly beyond the front edge of the waist stretchable region 79, which is to be pressed against the skin, so that leakage through the back laid-down portion 67b may occur. In contrast, as in the illustrated embodiment, with the waist elastic members 71 provided in the first area 10 and the second area 20 (i.e., the front edges of the back laid-down portions 67b are located on or backward of the front edge of the waist stretchable region 79), not the back laid-down portion 67b, which has a poorer fitting property against the skin, but the standup portion 68, which has a higher fitting property against the skin, is present forward of the front edge of the waist stretchable region 79, which is to be pressed against the skin. Consequently, the second area 20 is raised and subsequently the standup portion 68 of each standup gather part 60 located in each of the opposed lateral edges of the second area 20 is raised, resulting in still more excellent leak protection property.

When the waist stretchable region 79 is provided over the first area 10 and the second area 20, it is preferred that, with a portion of the waist stretchable region 79 that is located in the second area 20 contracted in the width direction WD, ridges 80 extending from the first bending part 91 toward the second bending part 92 are formed repeatedly in the width direction WD on the top face of the second area 20, as shown in FIGS. 15, 18, and the like. In this way, the rigidity of the second area 20 is increased to make the reservoir space 21 hard to collapse. Further, with the ridges 80 that are extending from the first bending part 91 toward the second bending part 92 formed repeatedly in the width direction WD in the top face of the second area 20, even when the second area 20 falls toward the crotch side (over the region containing the absorber body 56), the reservoir space 21 is maintained to some extent due to the gaps 81 between the adjacent ridges 80 as shown in FIGS. 15(a), 15(b).

The distance in the front-back direction LD between the first bending part 91 and the second bending part 92 (equivalent to the dimension in the front-back direction LD of the second area 20), which affects the depth of the reservoir space 21 to be formed, may suitably be decided depending on the products. For example, usually, the distance in the front-back direction LD between the first bending part 91 and the second bending part 92 may be 10 to 40 mm, particularly 20 to 30 mm.

The position in the front-back direction LD of the front edge of the waist stretchable region 79 may suitably be decided, and usually the distance in the front-back direction LD between the front edge of the waist stretchable region 79 and the back edge of the absorber body 56 is preferably 0.2 to 0.5 times the dimension in the front-back direction LD of the end flap EF. Further, the distance 79a between the front edge of the waist stretchable region 79 and the front edges of the back laid-down portions 67b may suitably be decided, and is preferably 0 to about 15 mm.

It suffices that the waist stretchable region 79 is provided only in part of the region between the right and left back laid-down portions 67b, as long as the waist stretchable region 79 is formed at least between the right and left back laid-down portions 67b in the end flap EF. However, with the waist stretchable region 79 extending at least up to the right and left back laid-down portions 67b as in the illustrated embodiment, the portion located between the right and left standup gather parts 60 and backward of the second area 20 is brought into close contact with the skin of the wearer over the entire width WD. Accordingly, the leak protection property is still more improved, which is preferable. From a similar standpoint, the distance 79b in the front-back direction LD between the back edge of the waist stretchable region 79 and the back edge of the end flap EF is preferably 17 mm or shorter.

The gathering elastic members 63 may not be positioned above the absorber body 56 in the spread state, but when at least the gathering elastic members 63 attached to the leading edge portion of each standup portion 68 are positioned above the absorber body 56, the contracting force of the gathering elastic members 63 of the standup gather parts 60 more directly acts on the second area 20 to facilitate raising of the second area 20 from the back edge of the absorber body 56 as the stand-up line, which is preferable.

As in the embodiment illustrated in FIG. 10, when the front edge of the back laid-down portion 67b is located backward of the front edge of the waist stretchable region 79, and a stretchable sheet 70 having four or more identical, elongate waist elastic members 71 attached thereto at intervals in the front-back direction LD is used, it is preferred that a plurality of first waist elastic members 71a located in the area between the front edge of the back laid-down portion 67b and the front edge of the waist stretchable region 79 and a plurality of second waist elastic members 71b located in the remaining area are separately provided, and that the intervals in the front-back direction LD between the first waist elastic members 71a 0.4 to 0.6 times the intervals in the front-back direction LD between the second waist elastic members 71b. In this way, creases extending in the longitudinal direction are formed in the portion of the second area 20 coincident with the waist stretchable region 79, and the rigidity is increased by compression to make the reservoir space 21 to be formed hard to collapse, which is preferable.

Further, as in the embodiment illustrated in FIG. 8, when the front edge of the back laid-down portion 67b is located backward of the front edge of the waist stretchable region 79, and a stretchable sheet 70 having four or more identical, elongate waist elastic members 71 attached thereto at intervals in the front-back direction LD is used, all of the waist elastic members 71 may have the same stretch rate, some of the waist elastic members 71 may have a stretch rate different from that of the other waist elastic members 71, or all of the waist elastic members may have different stretch rates. For example, it is preferred that the first waist elastic members 71a located in the area between the front edges of the back laid-down portions 67b and the front edge of the waist stretchable region 79 and the second waist elastic members 71b located in the remaining area are separately provided, and that the stretch rate of the first waist elastic members 71a is 1.05 to 1.15 times the stretch rate of the second waist elastic members 71b. In this way, creases extending in the longitudinal direction are also formed in the portion of the second area 20 coincident with the waist stretchable region 79, and the rigidity is increased by compression to make the reservoir space 21 to be formed hard to collapse, which is preferable.

As in the illustrated embodiment, when a stretchable sheet 70 having a plurality of elongate waist elastic members 71 attached thereto at intervals in the front-back direction LD is used, an edge portion without a waist elastic member 71 is inevitably formed in the front edge portion of the stretchable sheet 70. Here, as in the embodiment illustrated in FIG. 11, when the back end portion of the absorber body 56 and the edge of the front end portion of the stretchable sheet 70 overlap (the back edge of the absorber body 56 may be coincident with the front edge of the stretchable sheet 70), the stretchable sheet 70 is present all over the front-back direction LD of the second area 20, resulting in improved rigidity. Consequently, the second area 20 is securely raised to make the reservoir space 21 hard to collapse. Further, with a gap between the front edge of the stretchable sheet 70 and the back edge of the absorber body 56, some user may recognize the gap as being thin in thickness and easy to cause leakage, but with the back end portion of the absorber body 56 and the edge of the front end portion of the stretchable sheet 70 overlapping, the resulting appearance will not make the user insecure, which is preferable.

The second area 20 is preferably an area exclusive of the absorber body 56 as in the embodiment illustrated in FIG. 8 and the like, for little increase in thickness even when the second area 20 falls toward the crotch side along the second bending part 92. Alternatively, as in the embodiment illustrated in FIG. 26, the second area 20 may be provided with an auxiliary absorber body 56B separate from the primary absorber body 56A provided in a third area 33 adjacent forward to the second bending part 92, to thereby enhance the rigidity of the second area 20. In this way, the second area 20 is securely raised to make the reservoir space 21 hard to collapse, and liquid portion of the bodily waste introduced into the reservoir space 21 may be absorbed and held in the auxiliary absorber body 56B in the second area 20. The auxiliary absorber body 56B may be made of the same material and may have the same structure as the primary absorber body 56A.

<First Bend>

The first bending part 91 is preferably a zone that has lower rigidity and is thus easier to bend compared to the first area 10 and the second area 20. In this way, the bending position of the first bending part 91 is hard to be displaced forward, which facilitates retention of the shape and position of the reservoir space 21. Even when the bending position is displaced forward of the first bending part 91 by external force temporarily applied during use or product packaging to form a slight inadvertent folding line, the first bending part 91 is still easier to bend, and thus the bending position is returned to the first bending part upon release from the external force to retain the shape and position of the reservoir space 21. Note that the rigidity of each part may be determined by Gurley's method as disclosed in Patent Literature 1.

The first bending part 91 is a linear zone extending in the width direction WD from the front edge of one of the back laid-down portion 67b to the front edge of the other of the back laid-down portion 67b, and its dimension in the front-back direction LD may suitably be decided. The dimension in the front-back direction LD of the first bending part 91 is preferably small, usually about 1 to 3 mm, and in the illustrated embodiment, preferably smaller than the intervals in the front-back direction LD between the elastic members.

Means for imparting lower rigidity to the first bending part 91 compared to the first area 10 and the second area 20 is not particularly limited, and the following two means are typically conceivable.

The first means makes use of enhancement of rigidity by joining means, such as hot melt adhesives or melt-bonding, to reduce the joining amount (amount of adhesives or melt-bonded amount) in the first bending part 91 compared to those in the first area 10 and the second area 20. FIG. 8 shows a specific embodiment intended for the structure wherein the waist elastic member is a plurality of elongate waist elastic members 71 each extending in the width direction WD and arranged at intervals in the front-back direction LD, the first area 10 and the second area 20 each contain at least one of the waist elastic members 71, and the first sheet layer 73 adjacent to the top side of the waist elastic members 71 and the second sheet layer 74 adjacent to the underside of the waist elastic members 74 are provided. That is, in this embodiment, joined zones 75 of the first sheet layer 73 and the second sheet layer 74 extending backward from the vicinity of the first bending part 91 crossing the waist elastic members 71 and unjoined zones 77 of the first sheet layer 71 and the second sheet layer 74 extending forward from the vicinity of the first bending part 91 crossing the waist elastic members 71 are provided alternately and repeatedly in the width direction WD in the first area 10 and the second area 20. The first bending part 91 is free of the joined zones 75.

With such a structure, the portion containing the joined zones 75 has a relatively higher rigidity, whereas the portion without the joined zones 75 has a relatively lower rigidity. As a result, a first bending part 91 with lower rigidity may be formed with a simple structure using a particular pattern of the joined zones 75. On the other hand, higher rigidity is imparted to the second area 20 by contraction in the width direction WD, which further improves the rentainability of the reservoir space 21. For improved rigidity, the joined zones 75 are preferably formed by melt-bonding the first sheet layer 73 and the second sheet layer 74.

The second means is to employ a smaller number of stacked member layers in the first bending part 91 compared to those in the first area 10 and the second area 20. FIG. 25 shows a specific embodiment wherein stretchable sheets 70A, 70B (with a structure shown in FIGS. 8 and 9, or may be made of urethane foam, elastic film, or the like) are disposed in the first area 10 and the second area 20, respectively, but these stretchable sheets are not placed in the first bending part 91, so that the number of the stacked member layers in the first bending part 91 is smaller than those in the first area 10 and the second area 20. In this case, the portion having the stretchable sheet 70A, 70B has a relatively higher rigidity, whereas the portion without the stretchable sheet 70A, 70B has a relatively lower rigidity. As a result, a first bending part 91 with lower rigidity may be formed with a simple structure. On the other hand, higher rigidity is imparted to the second area 20 by contraction in the width direction WD, which further improves the rentainability of the reservoir space 21.

Either one or both of the two means discussed above may be employed.

When the auxiliary absorber body 56B is provided in the second area, it is preferred for still less possibility of displacement of the bending position to position the back edge of the auxiliary absorber body 56B and the back edge of the second area 20 coincidently, which particularly increases the difference in rigidity between the first bending part 91 and the portion forward thereof.

<Second Bend>

The second bending part is preferably a zone that has lower rigidity and is thus easier to bend compared to the second area 20 and the third area 33 adjacent forward to the second bending part 92. In this way, the bending position of the second bending part 92 is hard to be displaced forward, which facilitates retention of the shape and position of the reservoir space 21. Even when the bending position is displaced backward of the second bending part 92 by external force temporarily applied during use or product packaging to form a slight inadvertent folding line, the second bending part 92 is still easier to bend, and thus the bending position is returned to the second bending part upon release from the external force to retain the shape and position of the reservoir space 21. Note that the rigidity of each part may be determined by Gurley's method as disclosed in Patent Literature 1.

The second bending part 92 is a linear zone extending in the width direction WD and spaced forwardly apart from the first bending part 91, and its dimension in the front-back direction LD may suitably be decided. The dimension of the front-back direction LD of the second bending part 92 is preferably small, usually about 1 to 3 mm, and in the illustrated embodiment, preferably smaller than the intervals in the front-back direction LD between the waist elastic members 71.

Means for imparting lower rigidity to the second bending part 92 compared to the second area 20 is not particularly limited, and the following three means are typically conceivable.

The first means makes use of enhancement of rigidity by joining means, such as hot melt adhesives or melt-bonding, to impart lower rigidity to the second bending part 92 compared to the second area 20. FIG. 8 shows a specific embodiment intended for the structure wherein the waist elastic member is a plurality of elongate waist elastic members 71 each extending in the width direction WD and arranged at intervals in the front-back direction LD, the first area 10 and the second area 20 each contain at least one of the waist elastic members 71, and the first sheet layer 73 adjacent to the top side of the waist elastic members 71 and the second sheet layer 74 adjacent to the underside of the waist elastic members 74 are provided. In this embodiment, joined zones 75 of the first sheet layer 73 and the second sheet layer 74 extending continuously backward from the front edge of the second area 20 crossing the waist elastic members 71 and unjoined zones 77 of the first sheet layer 71 and the second sheet layer 74 extending continuously backward from the front edge of the second area 20 crossing the wait elastic members 71 are provided alternately and repeatedly in the width direction WD in the second area 20.

With such a structure, the front edges of the joined zones 75 are located on the front edge of the second area 20, and the portion containing the joined zones 75, i.e., the portion adjacent backward to the second bending part 92, has a relatively higher rigidity in the presence of the joined zones 75. As a result, the rigidity of the second area 20 may be made higher than that of the second bending part 92 with a simple structure using a particular pattern of the joined zones 75. Further, higher rigidity is imparted to the second area 20 also by contraction in the width direction WD, which further makes the reservoir space 21 hard to collapse.

The second means is to employ a smaller number of stacked member layers in the second bending part 92 compared to that in the second area 20 to impart lower rigidity to the second bending part 92 compared to the second area 20. FIG. 25 shows a specific embodiment wherein the stretchable sheet 70B (with a structure shown in FIGS. 8 and 9, or may be made of urethane foam, elastic film, or the like) is disposed in the second area 20, the front edge of the stretchable sheet 70B is coincident with the front edge of the second area 20, and the second bending part 92 is free of the stretchable sheet 70B.

With such a structure, the portion where the stretchable sheet 70B is located, i.e., the portion adjacent backward to the second bending part 92, has a relatively higher rigidity in the presence of the stretchable sheet 70B. Thus, the rigidity of the second area 20 may be made higher than that of the second bending part 92 with a simple structure using a particular arrangement of the stretchable sheet 70B. Further, higher rigidity is imparted to the second area 20 also by contraction in the width direction WD, which further makes the reservoir space 21 hard to collapse.

The third means makes use of enhancement of rigidity by the absorber body 56 in the second area 20 to impart lower rigidity to the second bending part 92 compared to that of the second area 20. FIG. 26 shows a specific embodiment wherein the auxiliary absorber body 56B is provided in the second area 20, with the front edge of the auxiliary absorber body 56B coincident with the front edge of the second area 20. The second bending part 92 is positioned between the primary absorber body 56A and the auxiliary absorber body 56B, and exclusive of any absorber body. With such a structure, the portion where the auxiliary absorber body 56B is located, i.e., the portion adjacent backward to the second bending part 92, has a relatively higher rigidity in the presence of the auxiliary absorber body 56B. Thus, the rigidity of the second area 20 may be made higher than that of the second bending part 92 with a simple structure using the auxiliary absorber body 56B.

Any one or a plurality of the three means discussed above may be employed.

Means for imparting lower rigidity to the second bending part 92 compared to the third area 33 is not particularly limited, and it is preferred, as in the illustrated embodiment, to make use of enhancement of rigidity by the absorber body 56 in the third area 33 to impart lower rigidity to the second bending part 92 compared to that of the third area 33. That is, in the embodiment shown in FIG. 8 and the like, the back edge of the absorber body 56 (or the primary absorber body 56A in the embodiment shown in FIG. 26) is coincident with the back edge of the third area 33, and the second bending part 92 is exclusive of the absorber body 56. In this case, the third area 33 including the absorber body 56 has a relatively higher rigidity, whereas the second bending part 92 exclusive of the absorber body 56 has a relatively lower rigidity, so that the rigidity of the third area 33 may be made higher than that of the second bending part 92 with a simple structure using a particular arrangement of the absorber body 56.

<Direction of Ridges>

As in the stretchable sheet 70 shown in FIGS. 8, 9, and the like, the opposed lateral edges of the unjoined zones 77 and the joined zones 75 may extend linearly along the front-back direction LD, but it is also preferred, as shown in in FIGS. 18, 20(a), 21, and 23, that at least one unjoined zone 77 has opposed lateral edges with oblique portions 72 extending at an inclination angle θ (the angle of intersection on the acute angle side, the same is applied to the other inclination angles) of 5 to 45 degrees with respect to the front-back direction LD. It is more preferred that the inclination angle θ of the oblique portions 72 is 8 to 15 degrees. Here, the opposed lateral edges 77s of the unjoined zones 77 are defined by the lateral edges of the joined zones 75. Accordingly, when the joined zones 75 extend continuously from forward of the waist stretchable region 79 to backward thereof as illustrated in FIGS. 20 to 22, the opposed lateral edges 77s of the unjoined zones 77 refer to the lateral edges of the joined zones 75 in the spread state. Further, when the joined zones 75 extend intermittently (in dotted line) from forward of the waist stretchable region 79 to backward thereof as illustrated in FIGS. 23 and 24, the opposed lateral edges of the unjoined zones 77 correspond to the phantom lines linearly connecting the lateral edges of the joined zones 75 in the spread state in the extending direction of the ridges 80. Further, when the inclination angle θ of the opposed lateral edges 77s of the unjoined zones 77 with respect to the front-back direction LD varies continuously, for example, when the opposed lateral edges 77s of the unjoined zones 77 form curved lines, such as of an arcuate shape as in the embodiment illustrated in FIG. 20(d), the direction of the opposed lateral edges 77s of the unjoined zones 77 refers to the direction of the tangent line of the opposed lateral edges 77s of the joined zones 75, The opposed lateral sides of at least part of the ridges 80 formed in the top face of the waist stretchable region 79 are, in the locations corresponding to the oblique portions 72 of the unjoined zones 77, slanted in generally the same direction along the opposed lateral edges 77s of the unjoined zones 77, so that urine or loose stool intruded into the gaps 81 between the adjacent ridges 80, when migrates in the front-back direction LD, impinges on the slanted ridges 80 to produce migration resistance. And the gaps 81 between the adjacent ridges 80 are made to extend continuously from forward of the waist stretchable region 79 to backward thereof like the ridges 80, so that air permeability in the first area 10, which is to be brought into close contact with the skin, is not impaired. Further, the ridges 80 in the waist stretchable region 79 are communicated with the depression, which is the reservoir space 21, so that when the volume of the depression, which is the reservoir space 21, is reduced by the external pressure (generated when the wearer takes the seated posture, supine position, or the like), the air in the depression is extruded through the gaps 81 between the adjacent ridges 80 in the first area 10, whereas when the volume of the depression, which is the reservoir space 21, is increased by release of the external pressure, the external air is introduced into the depression through the gaps 81 between the adjacent ridges 80 in the first area 10 (pumping action), so that the leak protection property is improved as discussed above while excellent air permeability is provided.

In view of the above, in the illustrated embodiment, it is preferred that at least all of the unjoined zones 77 in the waist stretchable region 79 located between the standup gather parts 60 have the oblique portions 72, and it is preferred that all of the unjoined zones 77 located in the region from the back laid-down portion 67b of one of the standup gather parts 60 to the back laid-down portion 67b of the other of the standup gather parts 60 have the oblique portions 72. It is indisputable that unjoined zones 77 having the oblique portions 72 and unjoined zones 77 without the oblique portions 72 may be arranged alternately, or one of them may be arranged every plurality of the other.

Each unjoined zone 77 may be formed with the oblique portions 72 in its entirety as shown in FIGS. 20(a) and 20(b), or may only partially have the oblique portions 72 as shown in FIGS. 20(c) and 20(d). It is preferred that the unjoined zones 77 at least in the first area 10 have the oblique portions 72, and particularly preferred that the unjoined zones 77 only in the first area 10 have the oblique portions 72, though not shown.

It is preferred that, as in the embodiment illustrated in FIG. 20(a), with the unjoined zones 77 with the oblique portions 72 repeatedly formed from rightward of the center of the width direction WD toward leftward of the center of the width direction WD, when the oblique portions 72 on the right and the oblique portions 72 on the left are respectively slanted toward the center of the width direction WD with increasing proximity to the waist, the ridges 80 are formed symmetrically to provide excellent appearance, which is preferable. It is indisputable that, as in the embodiment illustrated in FIG. 20(c), the oblique portions 72 on the right and the oblique portions 72 on the left are respectively slanted away from the center of the width direction WD with increasing proximity to the waist.

It is preferred that the ridges 80 are formed symmetrically as in the embodiments illustrated in FIGS. 20(a) and 20(c), where misalignment of the ridges 80 in the width direction WD would rather impair the appearance. Besides, such precise positioning of the ridges 80 are often difficult in the production. As such, it is conceivable that as in the embodiments illustrated in FIGS. 20(b) and 20(d), all of the unjoined zones 77 in the waist stretchable region 79 have the oblique portions 72 parallel to each other. In this way, through without symmetry, the ridges 80 are arranged in order, and slight misalignment of the ridges 80 in the width direction WD will affect little the appearance.

Among the unjoined zones 77 with the oblique portions 72, only the oblique portions 72 at constant angle suffice as in the embodiments illustrated in FIGS. 20(*a*) and 20(*b*), but it is preferred that the angles of the opposed lateral edges of the unjoined zones 77 vary with respect to the front-back direction LD in at least one location in the region from forward of the waist stretchable region 79 to backward thereof, as in the embodiments illustrated in FIGS. 20(*c*) and 20(*d*).

For example, in the embodiment illustrated in FIG. 20(*c*), the unjoined zones 77 with the oblique portions 72 have a first part P1 wherein the oblique portions 72 extend at an inclination angle θ of 5 to 45 degrees with respect to the front-back direction LD, and a second part P2 wherein the oblique portions 72 extend at an inclination angle γ of 5 to 45 degrees with respect to those in the first part P1. With such first part P1 and second part P2, even when the direction of the migration force applied to urine or loose stool intruded into the gaps 81 is closer to the direction of either of the parts P1, P2 (liable to pass along those oblique portions 72), the direction of the other of the parts P1, P2 is not closer to the direction of the migration force compared to the one, so that the other produces more effective resistance to the migration of urine or loose stool. The second part P2 may or may not have the inclination angle θ of 5 to 45 degrees with respect to the front-back direction LD (0 degree in the illustrated embodiment).

Further, in the embodiment illustrated in FIG. 20(*d*), the opposed lateral edges of each unjoined zone 77 have a continuously varying inclination angle δ all over the length with respect to the front-back direction LD, i.e., have a curved shape, such as an arcuate shape. In this way, even when the direction of the migration force applied to urine or loose stool intruded into the gaps 81 is closer to the direction of one location of the gaps 81 (liable to pass that location), the direction of the migration force is not closer to the direction of the other locations of the gaps 81, so that the other locations produces more effective resistance to the migration of urine or loose stool. Thus, the leak protection property discussed above is further enhanced.

For both enhanced air permeability and enhanced leak protection property, the rigidity of the ridges 80 formed in the waist stretchable region 79 is preferably higher. Accordingly, the stretchable sheet 70 is preferably interposed between any suitable members placed between the top sheet 30 and the exterior nonwoven sheet 12 as in the embodiment illustrated in FIGS. 7 to 9(*a*), rather than being placed as the top-most layer to be located closest to the skin as in the embodiment illustrated in FIGS. 12 to 15 or the embodiment illustrated in FIGS. 16 to 17. That is, one or a plurality of cover sheet layers (in the illustrated embodiment, the intermediate sheet 40 and the top sheet 30) are preferably provided above the first sheet layer 73 and, in this case, the cover sheet layer is joined to the first sheet layer 73 as shown in dash-dot line in FIGS. 22(*b*) and 22(*c*), and the first sheet layer 73 and the cover sheet layer integrally contract to form the ridges 80 in the top face (formed of the cover sheet layer) of the waist stretchable region 79.

<Nonwoven Fabric>

As the nonwoven fabric in the description hereinabove, commonly known nonwoven fabric may suitably be used depending on the parts or purposes. Examples of the constituent fibers of the nonwoven fabric include, but not limited to, synthetic fibers, such as polyolefin-based, e.g., polyethylene or polypropylene, polyester-based, or polyamide-based fibers (including not only single component fibers, but also composite fibers, such as of core/sheath type), as well as regenerated fibers, such as rayon or cupra, or natural fibers, such as cotton, and also mixtures thereof. For improved flexibility of the nonwoven fabric, the constituent fibers may preferably be crimped fibers. The constituent fibers of the nonwoven fabric may also be hydrophilic fibers (including those rendered hydrophilic with hydrophilizers), hydrophobic fibers, or water-repelling fibers (including those rendered water-repelling with water repellents). Further, nonwoven fabric may generally be categorized into discontinuous fiber nonwoven, continuous fiber nonwoven, spunbonded nonwoven, melt blown nonwoven, spunlace nonwoven, thermal bonded (air through) nonwoven, needle-punched nonwoven, point-bonded nonwoven, composite nonwoven (SMS or SMMS nonwoven fabric having a melt blown layer interposed between spunbonded layers), or the like nonwoven fabric, generally depending on the length of the fibers, method of forming the sheet, method of joining the fibers, or layered structure, and any of these nonwoven fabric may be used.

<Explanation of Terms in the Specification>

The following terms appearing in the present specification shall have the following means unless otherwise specified herein.

The "front-back direction" refers to the direction shown by the reference sign LD (longitudinal direction) in the figures, whereas the "width direction" refers to the direction shown by the reference sign WD (right-left direction) in the figures, and the front-back direction and the width direction are orthogonal to each other.

The "MD" and "CD" refer to the flow direction (MD: machine direction) and the lateral direction orthogonal thereto (CD: cross direction) in the production facilities, respectively, and either one of these is aligned to the front-back direction while the other is aligned to the width direction, depending on the parts of the product. The MD of nonwoven fabric is the direction of fiber orientation in the nonwoven fabric. The fiber orientation refers to the direction along which the fibers of the nonwoven fabric are aligned, and may be identified, for example, by a measurement method pursuant to the fiber orientation testing method using zero-span tensile strength prescribed in TAPPI Standard Method T481, or by a simplified measurement method for determining the fiber orientation by the ratio of tensile strengths in the front-back direction and in the width direction.

The "top side" refers to the side, when the article is worn, closer to the skin of the wearer, whereas the "underside" refers to the side, when the article is worn, away from the skin of the wearer.

The "top face" refers to the face, when the article is worn, closer to the skin of the wearer, whereas the "under face" refers to the face, when the article is worn, away from the skin of the wearer.

The "stretch rate" refers to a value with respect to the natural length being 100%. For example, a 200% stretch rate is synonymous with stretch in two folds.

The "gel strength" is determined as follows. To 49.0 g of artificial urine (a mixture of 2 wt % urea, 0.8 wt % sodium chloride, 0.03 wt % calcium chloride dihydrate, 0.08 wt % magnesium sulfate heptahydrate, and 97.09 wt % ion-exchanged water), 1.0 g of superabsorbent polymer is added and stirred with a stirrer. The resulting gel is left in a chamber with constant temperature and humidity at 40° C. at 60% RH for 3 hours, and then the temperature is returned to the ordinary temperature.

The gel strength is measured in a curd meter (Curd-meter-MAX ME-500 manufactured by I. techno Engineering).

The "basis weight" is determined as follows. A specimen or test piece is preliminarily dried, left in a laboratory or in apparatus under the standard conditions (23±1° C. temperature and 50±2% relative humidity in the testing location) until constant mass is attained. The preliminary drying refers to attaining constant mass from a specimen or test piece in the environment at a temperature of 100° C. No preliminary drying may be performed on fibers with an official regain of 0.0%. From the test piece of the constant mass, a specimen of 100 mm×100 mm size is cut out using a sampling template (100 mm×100 mm). The weight of the specimen is measured and multiplied by 100 times to calculate the weight per 1 $m^2$, which is taken as the basis weight.

The "thickness" is automatically measured using an automatic thickness meter (KES-G5 handy compression tester program) under a load of 0.098 $N/cm^2$ with the compression area of 2 $cm^2$. The thickness of perforated nonwoven fabric is measured at a position other than the apertures and the protrusions thereamound.

The water absorption is determined in accordance with JIS K7223-1996 "Testing method for water absorption capacity of super absorbent polymers".

The water absorption rate is defined as the "time spent until the end point is reached" in carrying out JIS K7224-1996 "Testing method for water absorption rate of super absorbent polymers" using 2 g of superabsorbent polymer and 50 g of saline.

The "spread state" refers to the state in which an article is spread flatly without contraction or slack.

The size of each part refers to the size not in the natural length state but in the spread state, unless otherwise specified.

A test or measurement shall be, in the absence of description about environmental conditions, performed in a laboratory or in apparatus under the standard conditions (23±1° C. temperature and 50±2% relative humidity in the testing location).

INDUSTRIAL APPLICABILITY

The present invention is applicable to attachable-type disposable wearing articles, such as the tape-type disposable diapers as described above as examples.

DESCRIPTION OF REFERENCE SIGNS

B: dorsal section
EP: end flap
F: ventral section
LD: front-back direction
SF: side flap
WD: width direction
WP: wing
θ, γ: inclination angle
10: first area
11: liquid-impervious sheet
12: exterior nonwoven sheet
12T: target sheet
13: attaching tape
13A: attaching part
13B: body portion
13C: base portion
20: second area
21: reservoir space
30: top sheet
33: third area
40: intermediate sheet
50: absorbent element
56: absorber body
58: packing sheet
60: standup gather part
62: gathered sheet
63: gathering elastic member
65: root portion
66: main body portion
67b: back laid-down portion
67f: front laid-down portion
68: standup portion
70: stretchable sheet
71: waist elastic member
72: oblique portion
73: first sheet layer
74: second sheet layer
75: joined zone
76: fixing portion
77: unjoined zone
79: waist stretchable region
80: ridge
81: gap
91: first bending part
92: second bending part
56A: primary absorber body
56B: auxiliary absorber body

The invention claimed is:

1. An attachable-type disposable wearing article comprising:
    a crotch section containing a middle of front-back direction;
    a ventral section extending forward from the middle of the front-back direction;
    a dorsal section extending backward from the middle of the front-back direction;
    an absorber body contained in a region including the crotch section;
    an attaching part provided in each of opposed lateral portions of the dorsal section, and to be detachably attached to an exterior face of the ventral section;
    an end flap extending backward of a back edge of the absorber body;
    a waist elastic member fixed to the end flap; and
    standup gather parts which stand up from a top face along shielding positions of bodily waste on opposed lateral sides in the width direction,
    wherein a region containing the waist elastic member is contracted in the width direction together with the waist elastic member, and has a waist stretchable region stretchable in the width direction,
    wherein each of the standup gather parts has a root portion fixed outward in the width direction of a shielding position, a main body portion extending from the root portion, a front laid-down portion and a back laid-down portion formed by fixing a front end portion and a back end portion, respectively, of the main body portion in a laid down state, a standup portion formed by unfixing the main body portion between the front laid-down portion and the back laid-down portion, and a gathering elastic member attached at least to a free edge area of the standup portion, wherein at least the free edge area of the standup portion is contracted in the front-back direction together with the gathering elastic member and is stretchable in the front-back direction, wherein a linear first bending part extending in the width direction from a front edge of one of the back laid-down portions to a front edge of the other of the back laid-down portions and a linear second bending part extending in the width direction and spaced forwardly apart from the first bending part are provided, wherein a first area adjacent backward to the first bending part and a second area between the first bending part and the second bending part are provided, wherein the waist stretchable region is provided at least between the opposed right and left back laid-down portions, wherein the first bending part has lower rigidity compared to the first area and the second area, and wherein, as the standup portions contract, the second area is raised along the second bending part as a stand-up line, and the first area is bent back along the first bending part with respect to the second area.

2. The attachable-type disposable wearing article according to claim 1, further comprising:

a first sheet layer adjacent to a top side of the waist elastic members, and a second sheet layer adjacent to an underside of the waist elastic members, wherein the waist elastic member is a plurality of elongate waist elastic members each extending in the width direction and arranged at intervals in the front-back direction, wherein the first area and the second area each contain at least one of the waist elastic members, wherein, in the first area and the second area, joined zones of the first sheet layer and the second sheet layer extending backward from a vicinity of the first bending part crossing the waist elastic members and unjoined zones of the first sheet layer and the second sheet layer extending forward from a vicinity of the first bending part crossing the waist elastic members are provided alternately and repeated in the width direction, and wherein the first bending part is free of the joined zones.

3. The attachable-type disposable wearing article according to claim 2, wherein a stretch rate of the waist elastic members in the spread state is 160 to 230%.

4. The attachable-type disposable wearing article according to claim 3, further comprising a stretchable sheet which includes the waist elastic members and the first and second sheet layers covering a top side and an underside thereof, and is attached to a region including the end flap, wherein the stretchable sheet has, in its front end portion, an edge portion without the waist elastic members, and wherein a front edge of the stretchable sheet extends forward at least to a front edge of the second area.

5. The attachable-type disposable wearing article according to claim 3, wherein the second area is exclusive of the absorber body.

6. The attachable-type disposable wearing article according to claim 3, wherein the absorber body comprises a primary absorber body provided in a third area adjacent forward to the second bending part, and an auxiliary absorber body provided in the second area, and wherein a back edge of the auxiliary absorber body is coincident with a back edge of the second area.

7. The attachable-type disposable wearing article according to claim 2, further comprising a stretchable sheet which includes the waist elastic members and the first and second sheet layers covering a top side and an underside thereof, and is attached to a region including the end flap, wherein the stretchable sheet has, in its front end portion, an edge portion without the waist elastic members, and wherein a front edge of the stretchable sheet extends forward at least to a front edge of the second area.

8. The attachable-type disposable wearing article according to claim 2, wherein the second area is exclusive of the absorber body.

9. The attachable-type disposable wearing article according to claim 2, wherein the absorber body comprises a primary absorber body provided in a third area adjacent forward to the second bending part, and an auxiliary absorber body provided in the second area, and wherein a back edge of the auxiliary absorber body is coincident with a back edge of the second area.

10. The attachable-type disposable wearing article according to claim 1, further comprising a stretchable sheet which includes the waist elastic members and the first and second sheet layers covering a top side and an underside thereof, and is attached to a region including the end flap, wherein the stretchable sheet has, in its front end portion, an edge portion without the waist elastic members, and wherein a front edge of the stretchable sheet extends forward at least to a front edge of the second area.

11. The attachable-type disposable wearing article according to claim 10, wherein the second area is exclusive of the absorber body.

12. The attachable-type disposable wearing article according to claim 10, wherein the absorber body comprises a primary absorber body provided in a third area adjacent forward to the second bending part, and an auxiliary absorber body provided in the second area, and wherein a back edge of the auxiliary absorber body is coincident with a back edge of the second area.

13. The attachable-type disposable wearing article according to claim 1, wherein the second area is exclusive of the absorber body.

14. The attachable-type disposable wearing article according to claim 1, wherein the absorber body comprises a primary absorber body provided in a third area adjacent forward to the second bending part, and an auxiliary absorber body provided in the second area, and wherein a back edge of the auxiliary absorber body is coincident with a back edge of the second area.

* * * * *